US009468540B2

(12) United States Patent
Nagatsuka et al.

(10) Patent No.: US 9,468,540 B2
(45) Date of Patent: Oct. 18, 2016

(54) ARTICULATED MECHANISM, FINGER, AND HAND

(71) Applicant: THK CO., LTD., Tokyo (JP)

(72) Inventors: Masaki Nagatsuka, Tokyo (JP); Yoshimasa Endo, Tokyo (JP)

(73) Assignee: THK CO., LTD., Tokyo (JP)

( * ) Notice: Subject to any disclaimer, the term of this patent is extended or adjusted under 35 U.S.C. 154(b) by 0 days.

(21) Appl. No.: 14/421,704

(22) PCT Filed: Apr. 4, 2013

(86) PCT No.: PCT/JP2013/060339
§ 371 (c)(1),
(2) Date: Feb. 13, 2015

(87) PCT Pub. No.: WO2014/162562
PCT Pub. Date: Oct. 9, 2014

(65) Prior Publication Data
US 2016/0008146 A1    Jan. 14, 2016

(51) Int. Cl.
*B25J 15/08* (2006.01)
*A61F 2/58* (2006.01)
*B25J 15/00* (2006.01)
(Continued)

(52) U.S. Cl.
CPC .............. *A61F 2/583* (2013.01); *A61F 2/588* (2013.01); *A61F 2/68* (2013.01); *A61F 2/70* (2013.01);
(Continued)

(58) Field of Classification Search
CPC  B25J 15/0009; B25J 15/0028; B25J 15/022; B25J 15/08; B25J 15/086; A61F 2/583; A61F 2/586; A61F 2/588; A61F 2/68; A61F 2/70; A61F 2002/5039; A61F 2002/701; A61F 2220/0041; A61F 2220/0091; Y10S 901/39
USPC .................................................. 294/106, 198
See application file for complete search history.

(56) References Cited

U.S. PATENT DOCUMENTS 3,927,424 A *  12/1975  Itoh .................. B25J 15/022
                                              294/106
4,368,913 A *   1/1983  Brockmann ......... B25J 15/0266
                                              294/106
(Continued)

FOREIGN PATENT DOCUMENTS

JP    S5163596 A    6/1976
JP    63-144985 A   6/1988
(Continued)

OTHER PUBLICATIONS

International Search Report dated Jun. 4, 2013, issued in corresponding application No. PCT/JP2013/060339.

*Primary Examiner* — Dean Kramer
(74) *Attorney, Agent, or Firm* — Westerman, Hattori, Daniels & Adrian, LLP

(57) ABSTRACT

An articulated mechanism system includes a plurality of fingers (articulated mechanisms) arranged in parallel, each of which has a mounting member, a first digital part rotatably connected to the mounting member by a first connecting part, a second digital part rotatably connected to the first digital part by a second connecting part, and a first driving part rotatably connected to the second digital part by a fourth connecting part and connected to a third connecting part. By extruding the third connecting part toward the fourth connecting part, the first digital part and the second digital part are integrally rotated about the first connecting part, or the second digital part is rotated about the second connecting part when the rotation of the first digital part is blocked. The third connecting parts are driven by a single driving mechanism for the same distance and in the same direction at a time.

22 Claims, 14 Drawing Sheets

(51) Int. Cl.
  *A61F 2/68*  (2006.01)
  *A61F 2/70*  (2006.01)
  *A61F 2/50*  (2006.01)
(52) U.S. Cl.
  CPC .... B25J 15/0009 (2013.01); *A61F 2002/5039* (2013.01); *A61F 2002/701* (2013.01); *A61F 2220/0041* (2013.01); *A61F 2220/0091* (2013.01); *Y10S 901/39* (2013.01)

(56) References Cited

U.S. PATENT DOCUMENTS 5,200,679 A * 4/1993 Graham ............... B25J 15/0009
                                                          294/111

8,182,010 B2 * 5/2012 Lee ..................... B25J 15/0009
                                                          294/106

FOREIGN PATENT DOCUMENTS

| JP | S6423384 A | 2/1989 |
| JP | 8-126984 A | 5/1996 |
| JP | 2001-277175 A | 10/2001 |
| JP | 2002-103269 A | 4/2002 |
| JP | 2009-233790 A | 10/2009 |
| JP | 2010-247320 A | 11/2010 |
| JP | 2011-104752 A | 6/2011 |
| WO | 2008/026574 A1 | 3/2008 |

* cited by examiner

ARTICULATED MECHANISM, FINGER, AND HAND

FIELD OF THE INVENTION

The present application relates to an articulated mechanism, a finger, and a hand.

BACKGROUND

Conventionally, as an articulated mechanism for a prosthetic hand or a robotic hand (collectively referred to as "hand"), articulated mechanisms capable of carrying out substantially the same movements as human digital joints have been developed. For example, one of such conventional articulated mechanisms is a mechanism in which a plurality of digital parts (corresponding to respective bones of a finger, referred to as link members) are rotatably joined each other and each of the joined digital parts is driven by a driving means so that the respective digital parts are rotated at desired degrees (see, for example, Patent documents 1, 2, 3 and 4). As the driving means, a linear actuator, a motor, a fluid-pressure-operated actuator, or the like may be used.

On the other hand, when a human hand grasps an object, a plurality of fingers are flexed in respective different shapes such that the respective fingers touch the surface of the object with substantially the same pressures. For carrying out such movement with the aforementioned conventional articulated mechanism, it is required to provide driving means for driving each finger independently so that the respective fingers can be flexed at different angles (see, for example, Patent document 1) or alternatively, it is required to diverge force by single driving means into the plural fingers (see, for example, Patent document 2).

PRIOR ART DOCUMENTS

Patent Documents

Patent document 1: JP2011-104752A
Patent document 2: JP2001-277175A
Patent document 3: WO2008-26574
Patent document 4: JPH08-126984A

SUMMARY OF THE INVENTION

Problem to be Solved by the Invention

However, in a case that driving means is provided for each finger, it is impossible to downsize an articulated mechanism and a hand having the articulated mechanism because there are many driving means. Further, it disturbs the reduction in cost and/or weight.

On the other hand, in case that the force of the single driving means is diverged into the plural fingers, it is impossible to downsize an articulated mechanism and a hand having the articulated mechanism because a complex multiple-unit system composed of pulleys, gears, differential gears, and the like is required. Similarly, it also disturbs the reduction in cost and/or weight.

On the other hand, in an articulated mechanism of Patent document 3 (see FIG. 10 through FIG. 13), a middle one (intermediate member) and a distal one (distal member) of three digital parts composing one finger are both made of plates each of which is formed in a U-like shape opening toward the inside (palm side). Accordingly, a lower surface of a bottom of the U-like shape faces to the outside (back side) so that the lower surface does not function as a contact surface for grasping an object. Additional part functioning as the contact surface is required, thus increasing the number of parts, making the structure complex, and increasing the weight. Since a joint (second shaft portion) for rotatably connecting a driving member (first linkage) and the middle digital part (the intermediate member) is disposed below a joint (first hinge) for rotatably connecting a proximal digital part (proximal member) and the middle digital part (the intermediate member), thus increasing the height of the finger. Accordingly, there is a problem that it is impossible to reduce the height size of the articulated mechanism.

Furthermore, in an articulated mechanism of Patent document 4, three digital parts (linkage) are all made of plates each of which is formed in a U-like shape opening toward the outside (back side) so that a lower surface of a bottom of the U-like shape functions as a contact surface for grasping an object. However, fluid-pressure-operated actuators are provided outside of the respective fingers, thus increasing the height size of the fingers. Accordingly, there is not only a problem that it is impossible to reduce the height size of the articulated mechanism but also a problem of complex structure, large number of parts, and heavy weight.

The present invention was made in the light of the above described problems and an object of the present invention is to provide an articulated mechanism, of which a plurality of fingers can be flexed into different shapes, respectively according to the configuration of an object to be grasped, having simple structure, and capable of allowing reduction in size, cost and weight, and also provide a hand having the articulated mechanism.

Another object of the present invention is to provide an articulated mechanism capable of allowing reduction in height size and simplification of the structure and to provide a finger and a hand having the articulated mechanism.

Means for Solving the Problems

An articulated mechanism system according to the present invention is characterized by comprising a plurality of articulated mechanisms each of which has at least a mounting member, a first digital part of which proximal end portion is rotatably connected to the mounting member by a first connecting part, a second digital part of which proximal end portion is rotatably connected to a distal end portion of the first digital part by a second connecting part, and a first driving part of which distal end portion is rotatably connected to a proximal end portion of the second digital part by a fourth connecting part and of which proximal end portion is connected to a third connecting part for applying driving power, wherein by extruding the third connecting part toward the fourth connecting part, the first digital part and the second digital part are integrally rotated about the first connecting part or the second digital part is rotated about the second connecting part when the rotation of the first digital part is blocked, wherein the plurality of articulated mechanisms are arranged in parallel to each other, and the articulated mechanism system further comprises a single driving mechanism for driving the third connecting parts of the respective articulated mechanisms for the same distance and in the same direction so that the plurality of articulated mechanisms are driven at a time.

According to the articulated mechanism system, the first and second digital parts can be easily flexed in different shapes according to the configuration of an object to be grasped simply by driving the plural articulated mechanisms, arranged in parallel, at a time with the single driving mechanism. This makes the movement similar to the movement of a plurality of fingers of a human hand easy. Since only the single driving mechanism is employed which drives the third connecting parts of the respective articulated mechanisms for the same distance and in the same direction, it allows simple structure and also reduction in size, cost, and weight. It should be noted that the aforementioned "same direction" is a concept including various directions such as the same linear direction and the same rotational direction.

In the aforementioned articulated mechanism system, it is preferable that the second connecting part for connecting the second digital part to the first digital part is located on the inside of the fourth connecting part for connecting the first driving part to the second digital part. By this structure, the driving force of the first driving part linked to the driving mechanism is first transferred to the second digital part and then transferred to the first digital part, to apply torque about the first and second connecting parts to the first and second digital parts Further, the respective articulated mechanisms may further comprise a third digital part of which proximal end portion is rotatably connected to a distal end portion of the second digital part by a fifth connecting part, and a second driving part of which distal end portion is rotatably connected to a proximal end portion of the third digital part by a seventh connecting part and of which proximal end portion is rotatably connected to a distal end portion of the first driving part by a sixth connecting part or to a distal end portion of the first digital part by a sixth connecting part, wherein when the second digital part is rotated relative to the first digital part, the third digital part is rotated relative to the second digital part by the second driving part.

According to this structure, the third digital part can be rotated and flexed relative to the second digital part in conjunction with the rotation of the second digital part relative to the first digital part.

Further, at least one of the first, second, third, and fourth connecting parts of one of the articulated mechanisms may have a position different from that of the other articulated mechanism(s).

According to this structure, the respective digital parts can be flexed differently from each other by driving the third connecting parts of the respective articulated mechanisms at a time for the same distance and the same direction with the single driving mechanism even though the articulated mechanisms are not in contact with an object. For example, when a human hand grasps an object, generally the fifth finger is flexed first and other fingers follow. Such movement is achieved by the simple structure.

Furthermore, the driving mechanism may comprise a linkage member which is linked to the respective third connecting parts to reciprocatably move said third connecting parts at a time, and an actuator for driving the linkage member.

According to the structure that the third connecting parts are reciprocatably moved by the linkage member as mentioned above, it allows simple structure and also reduction in size, cost, and weight.

Moreover, the aforementioned articulated mechanism may compose a hand (an artificial hand or a robot hand).

On the other hand, an articulated mechanism according to the present invention is characterized by comprising at least a mounting member, a first digital part of which proximal end portion is rotatably connected to the mounting member by a first connecting part, a second digital part of which proximal end portion is rotatably connected to a distal end portion of the first digital part by a second connecting part, and a first driving part of which distal end portion is rotatably connected to a proximal end portion of the second digital part by a fourth connecting part and of which proximal end portion is rotatably connected to a third connecting part for applying driving power, wherein by extruding the third connecting part toward the fourth connecting part, the first digital part and the second digital part are integrally rotated about the first connecting part or the second digital part is rotated about the second connecting part when the rotation of the first digital part is blocked, wherein the first and second digital parts are each made of a plate formed in a U-like shape and are arranged such that lower surfaces of bottoms thereof face to the inside, wherein the fourth connecting part is disposed on a portion between the second connecting part and the proximal end of the second digital part, and wherein at least a part of the fourth connecting part enters into an opening formed in the outside of the first digital part and the fourth connecting part is exposed outwardly from the opening of the first digital part when the second digital part is flexed inwardly relative to the first digital part.

According to the aforementioned articulated mechanism, since the first and second digital parts are each made of a plate formed in a U-like shape and are arranged such that the lower surfaces of the bottom thereof face to the inside, these lower surfaces can function as contact surfaces to the object directly. This can simplify the structure and reduce the weight. Since the fourth connecting part is disposed on a portion between the second connecting part and the proximal end of the second digital part, the second and fourth connecting parts do not overlap each other in the vertical direction, thereby allowing reduction in height size of a portion around the second connecting part connecting the first and second digital parts. At the same time, a space inside the first digital part is utilized as a part of the space for pivotal movement of the fourth connecting part, thereby reducing the projecting amount (projecting dimension) of the fourth connecting part projecting outwardly from the opening of the first digital part when the second digital part is flexed inwardly relative to the first digital part. That is, even though the first and second digital parts take any position (opened or closed), this structure allows reduction in height size of the portion around the second connecting part connecting the first and second digital parts.

It is preferable that the aforementioned articulated mechanism further comprises a third digital part of which proximal end portion is rotatably connected to a distal end portion of the second digital part by a fifth connecting part, and a second driving part of which distal end portion is rotatably connected to a proximal end portion of the third digital part by a seventh connecting part and of which proximal end portion is rotatably connected to a distal end portion of the first digital part by a sixth connecting part, wherein when the second digital part is rotated relative to the first digital part, the third digital part is rotated relative to the second digital part by the second driving part, wherein the third digital part is made of a board formed in a U-like shape and is arranged such that a lower surface of a bottom thereof faces to the inside, wherein the sixth connecting part is disposed on a portion between the second connecting part and the distal end of the first digital part and is inserted into a sixth connecting part cutout formed in each back-side edge of right and left side wall portions of the second digital part, and wherein when the third digital part is flexed inwardly relative to the second digital part, the sixth connecting part gets out of the sixth connecting part cutout.

Since the third digital part is made of a plate formed in a U-like shape and is arranged such that the lower surface of the bottom thereof faces to the inside as mentioned above, similarly to the first and second digital parts, the lower surface can function as contact surface to the object directly. This can simplify the structure and reduce the weight. Since the sixth connecting part is disposed on a portion between the second connecting part and the distal end of the first digital part, the second and sixth connecting parts do not overlap each other in the vertical direction, thereby also allowing reduction in height size of a portion around the second connecting part connecting the first and second digital parts. In addition, the sixth connecting part cutout formed in the second digital part is disposed between the right and left side wall portions of the first digital part, thereby reducing the projecting amount (projecting dimension) of the sixth connecting part projecting outwardly from the second digital part. That is, even though the first and second digital parts take any position (opened or closed), this structure allows reduction in height size of the portion around the second connecting part connecting the first and second digital parts.

The present invention also provides a finger to which the aforementioned articulated mechanism is applied, and further provides a hand (an artificial hand or a robot hand) comprising a plurality of the fingers.

Effects of the Invention

According to the present invention, it is possible to flex a plurality of articulated mechanisms into different shapes according to the configuration of an object to be grasped, and to allow simplification of the structure, reduction in size, cost and weight of the articulated mechanisms.

Further, according to the present invention, it is possible to allow reduction in height size of digital parts and simplification of the structure.

DESCRIPTION OF EMBODIMENTS

Hereinafter, embodiments of the present invention will be described with reference to the drawings.

First Embodiment

Figure 1:
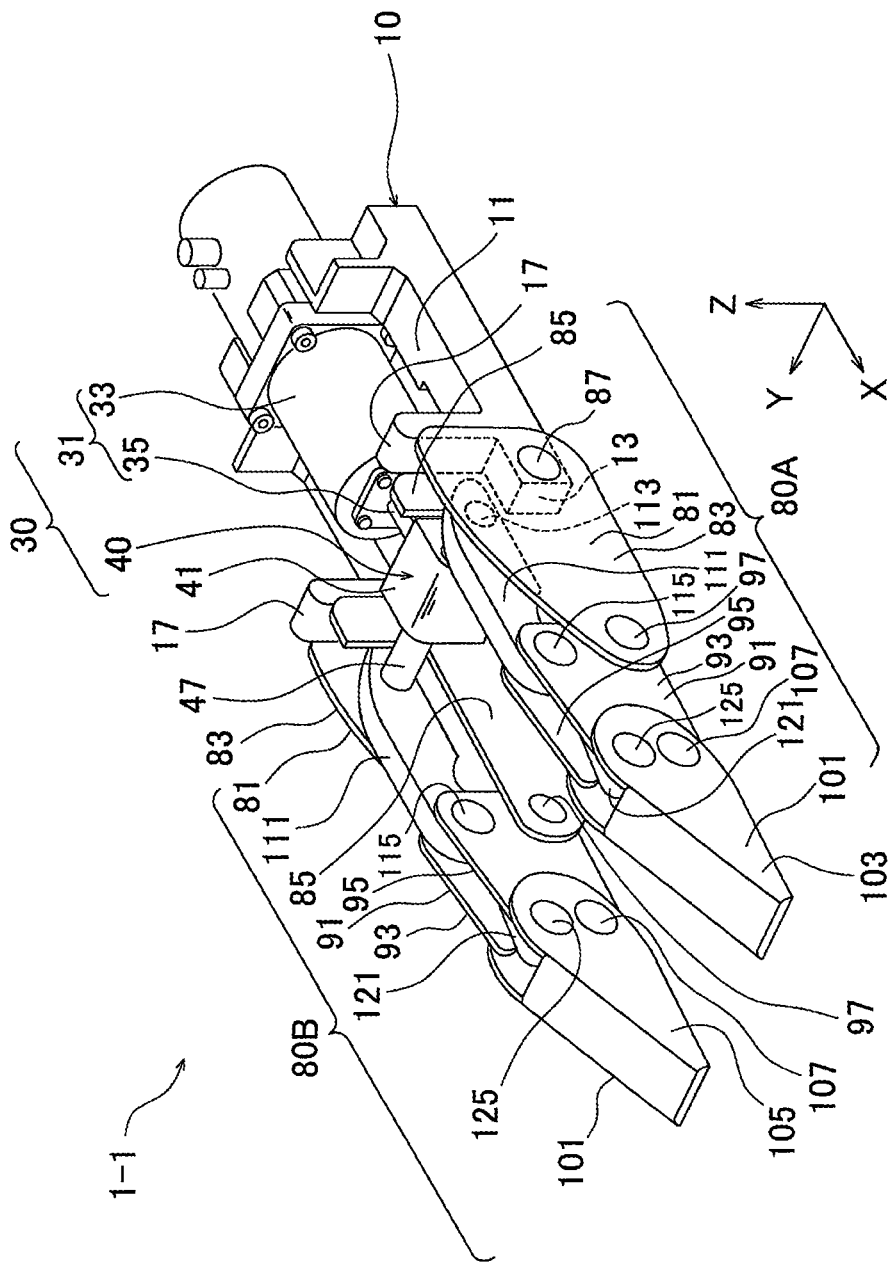
FIG. 1 is a perspective view of a hand 1-1.
Figure 2:
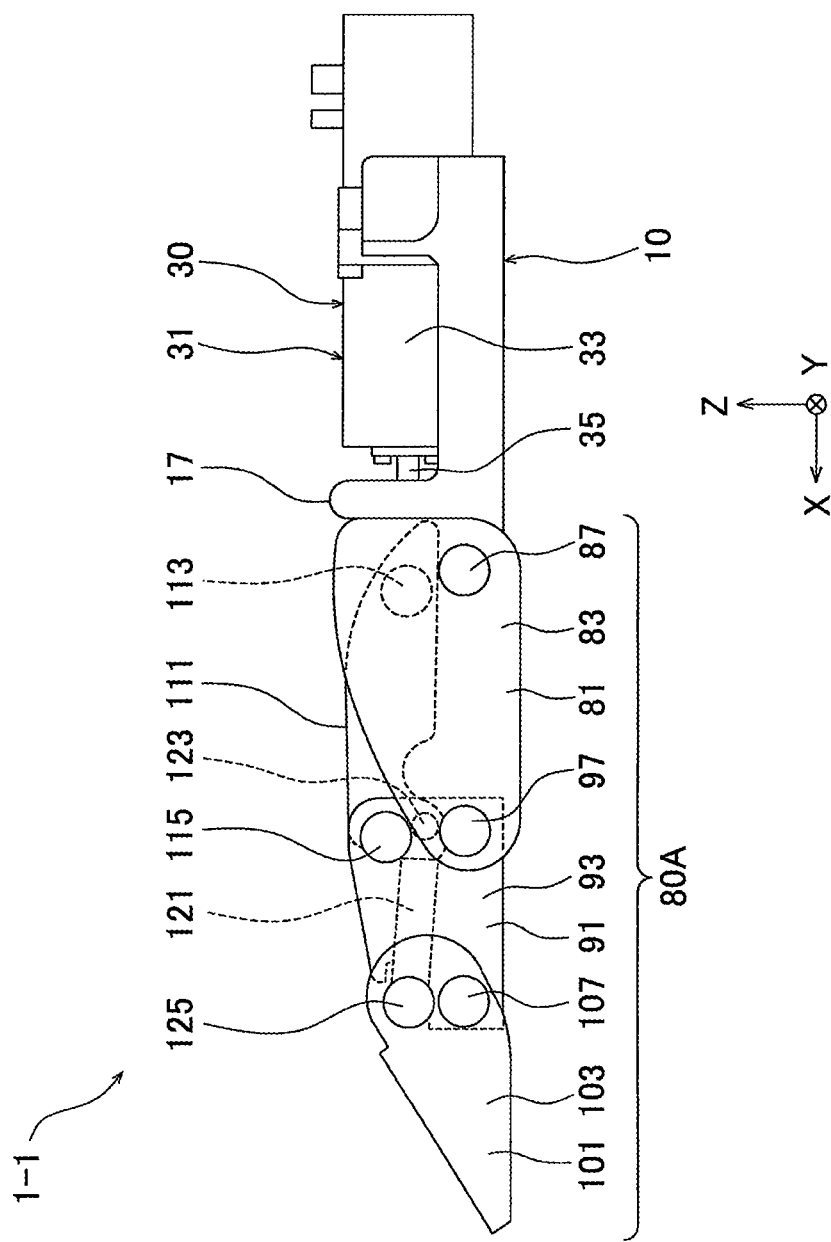
FIG. 2 is a side view of the hand 1-1.
Figure 3:
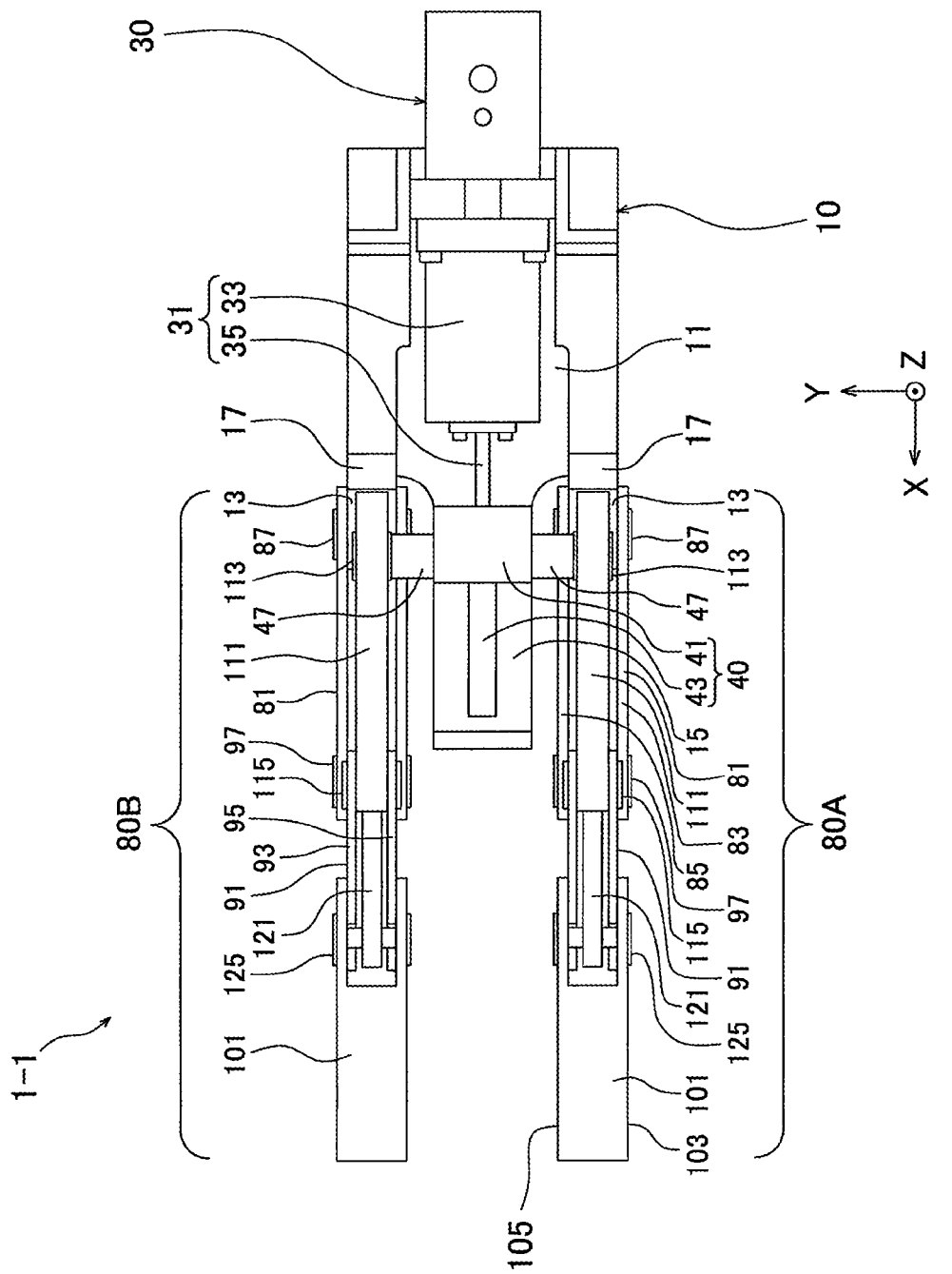
FIG. 3 is a plan view of the hand 1-1.

FIG. 1 is a perspective view of a hand 1-1 to which an articulated mechanism according to the first embodiment of the present invention is applied, FIG. 2 is a side view of the hand 1-1, and FIG. 3 is a plan view of the hand 1-1. As shown in these figures, the hand 1-1 comprises an mounting member (base member) 10, a driving mechanism 30 mounted to the mounting member 10, and a pair fingers 80A, 80B attached to the mounting member 10 and to be driven by the driving mechanism 30. In the following description, the side to which the fingers 80A, 80B are flexed (lower side in FIG. 1) is referred to inside or palm side and the other side (upper side in FIG. 1) is referred to outside or back side (the same as true for the other embodiments).

The mounting member 10 is substantially in a form of plate and its upper surface is a driving mechanism mounting surface 11. The mounting member 10 has digital part mounting portions 13 (only near side one is shown by dotted lines in FIG. 1) projecting from both sides of an end surface (front surface), on a side for installing the fingers 80A, 80B, of the mounting member 10 (the side indicated by arrow X in the figures). First digital parts 81 as described later are rotatably mounted to the digital part mounting portions 13. The mounting member 10 is provided with a rectangular slide member mounting portion 15 (see FIG. 3) projecting from the end surface, from which the digital part mounting portions 13 project, at a position between the digital part mounting portions 13. At roots of the digital part mounting portions 13, a pair of standing portions 17 project upward (in the direction shown by arrow Z) from the upper surface of the mounting member 10.

The driving mechanism 30 comprises a linear actuator 31 and a linkage member 40. The linear actuator 31 has a substantially cylindrical actuator body 33 and a rod 35 retractably projecting from one end of the actuator body 33. The linear actuator 31 is electric-powered to adjust the projecting amount of the rod 35. The actuator body 33 is fixed at the center of the driving mechanism mounting surface 11 of the mounting member 10 such that the rod 35 projects toward the linkage member 40 (in the direction of arrow X).

The linkage member 40 interlinks the linear actuator 31 and the two fingers 80A, 80B. As the linkage member 40, a linear guide is used in this embodiment. The linkage member 40 comprises the slide member 41 and a rail 43 (see FIG. 3). The slide member 41 is a substantially rectangular block and is disposed on a slide member mounting portion 15 of the mounting member 10. The end of the rod 35 is attached to one side of the slide member 41. The rail 43 is linear and is fixed to the slide member mounting portion 15 to extend in the sliding direction of the slide member 41 (the direction of arrow X). The slide member 41 is guided by the rail 43 to slide linearly and reciprocatably. That is, by driving the linear actuator 31, the slide member 41 is moved to slide along the rail 43 via the rod 35. A pair of shaft portions 47 projects from the right and left sides of the slide member 41 (the direction of arrow Y). The ends of the shaft portions 47 are rotatably connected to a third connecting part 113 of a first driving part 111 which will be described later.

Since the fingers 80A, 80B have the same structure, description will be made mainly as regard to one of the fingers 80A. The finger 80A comprises a first digital part 81 rotatably disposed on the mounting member 10, a second digital part 91 rotatably disposed on the first digital part 81, a third digital part 101 rotatably disposed on the second digital part 91, and first and second driving parts 111, 121 for driving the first, second, and third digital parts 81, 91, 101.

The first digital part 81 is made of a plate and formed by folding a lower portion of the plate into a U-like shape such that both walls of the U-like shape become parallel to each other. The pair of parallel walls are referred to as first digital body portions 83, 85, respectively. That is, the both first digital body portions 83, 85 are connected via a bottom plate.

The first digital body portion 85 located inside is formed in a substantially L-like shape, i.e. an upper portion of the first body portion 85 is cut off, not to disturb the movement of the shaft portion 47. Since there is no limitation on the first digital body portion 83 located outside, the first digital body portion 83 is larger than the first digital body portion 85 to increase mechanical strength. At the proximal side of the first digital body portions 83, 85 (the side near the mounting member 10), the digital part mounting portion 13 of the mounting member 10 is sandwiched between the lower portions of the first digital body portions 83, 85. The first digital part 81 is rotatably connected to the mounting member 10 by a first connecting part 87 located at the portions sandwiching the digital part mounting portion 13. The first connecting part 87 is provided with a bearing.

The second digital part 91 is made of a plate and formed by folding a lower portion of the plate into a U-like shape such that both walls of the U-like shape become parallel to each other. The pair of parallel walls are referred to as second digital body portions 93, 95, respectively. That is, the both second digital body portions 93, 95 are connected via a bottom plate. The second digital body portions 93, 95 have substantially the same configurations.

At the proximal side of the second digital body portions 93, 95 (the side near the first digital part 81), the lower portions thereof are formed to have such a width as to fit in a space between the distal portions of the first digital body portions 83, 85 of the first digital part 81. The second digital part 91 is rotatably connected to the first digital part 81 by a second connecting part 97 located at the portions sandwiched by the first digital part 81. The second connecting part 97 is provided with a bearing.

The third digital part 101 is made of a plate and formed by folding an upper portion of the plate into an inverted U-like shape such that both walls of the inverted U-like shape become parallel to each other. The pair of parallel walls are referred to as third digital body portions 103, 105, respectively. That is, the both third digital body portions 103, 105 are connected via an upper plate. The third digital body portions 103, 105 have substantially the same configurations.

At the proximal side of the third digital body portions 103, 105 (the side near the second digital part 91), the lower portions thereof are arranged outside the distal portions of the pair of the second digital body portions 93, 95 of the second digital part 91 so as to sandwich them. The third digital part 101 is rotatably connected to the second digital part 91 by a fifth connecting part 107 located at the portions sandwiching the second digital part 91. The fifth connecting part 107 is provided with a bearing.

The first driving part 111 has a plate-like shape and is rotatably connected to an end of each shaft portion 47 of the slide member 41 by a third connecting part 113 at the proximal side of the first driving part 111 (the side near the mounting member 10). On the other hand, at the distal side of the first driving part 111 (the side near the second digital part 91), the first driving part 111 is rotatably connected to portions at the proximal side (above the second connecting part 97) of the second digital part 91 by a fourth connecting part 115. That is, the first driving part 111 is connected to the second digital part 91 by the fourth connecting part 115 and the first digital part 81 is connected to the second digital part 91 by the second connecting part 97 located on the inside of the fourth connecting part 115. The third connecting part 113 and the fourth connecting part 115 are provided with bearings, respectively.

The second driving part 121 has a plate-like shape and is rotatably connected to a distal end portion (below the fourth connecting part 115) of the first driving part 111 by a sixth connecting part 123 (see FIG. 2) at the proximal side of the second driving part 121 (the side near the first driving part 111). On the other hand, a distal end portion of the second driving part 121 (the side near the third digital part 101) is rotatably connected to a proximal end portion (above the fifth connecting part 107) of the third digital part 101 by a seventh connecting part 125. The sixth connecting part 123 and the seventh connecting part 125 are provided with bearings, respectively.

At predetermined positions, the fingers 80A, 80B are each provided with biasing means such as coil spring for biasing the digital parts 81, 91, 101 wholly in a broadening direction, but the biasing means are not illustrated.

Figure 4:
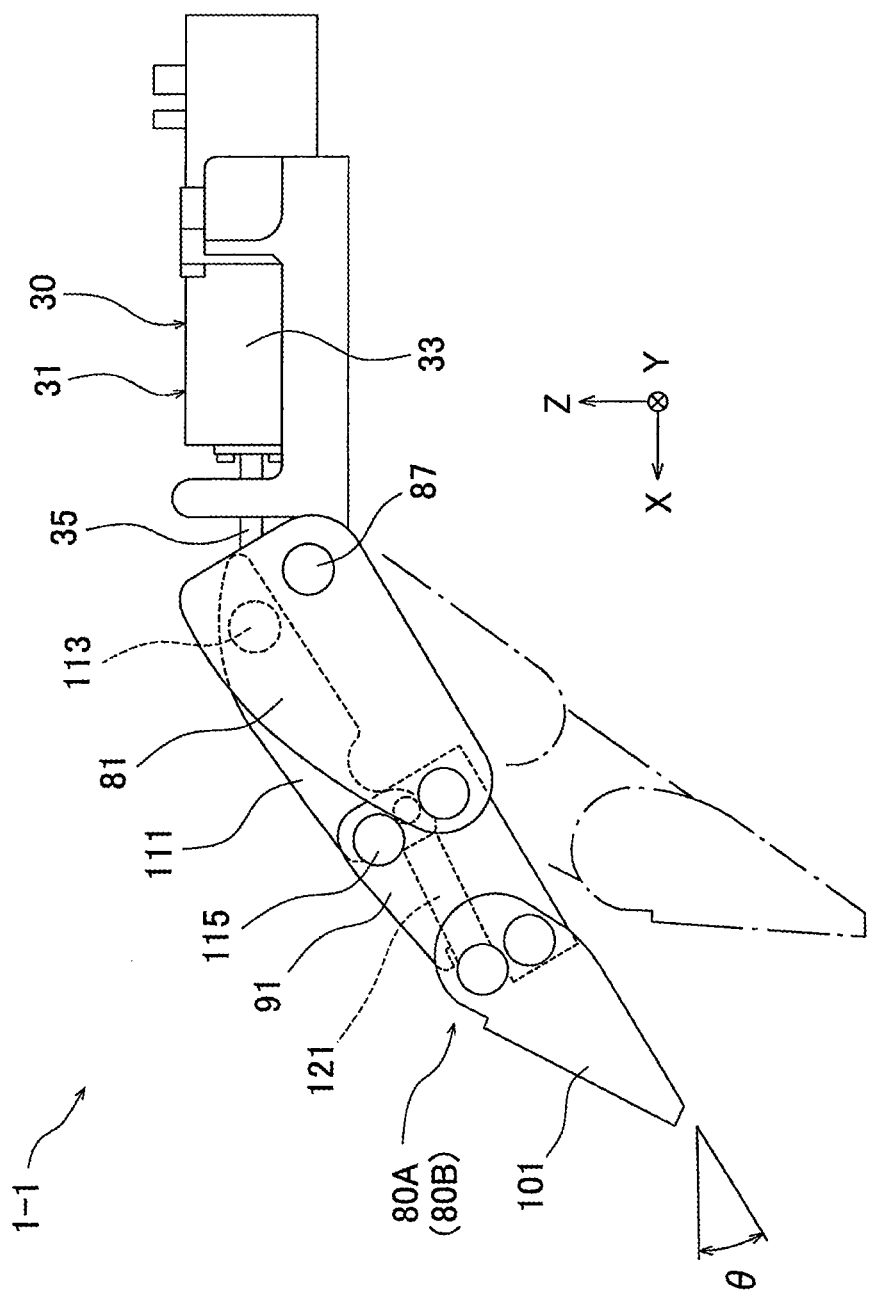
FIG. 4 is an illustration for explaining movement of the hand 1-1.
Figure 5:
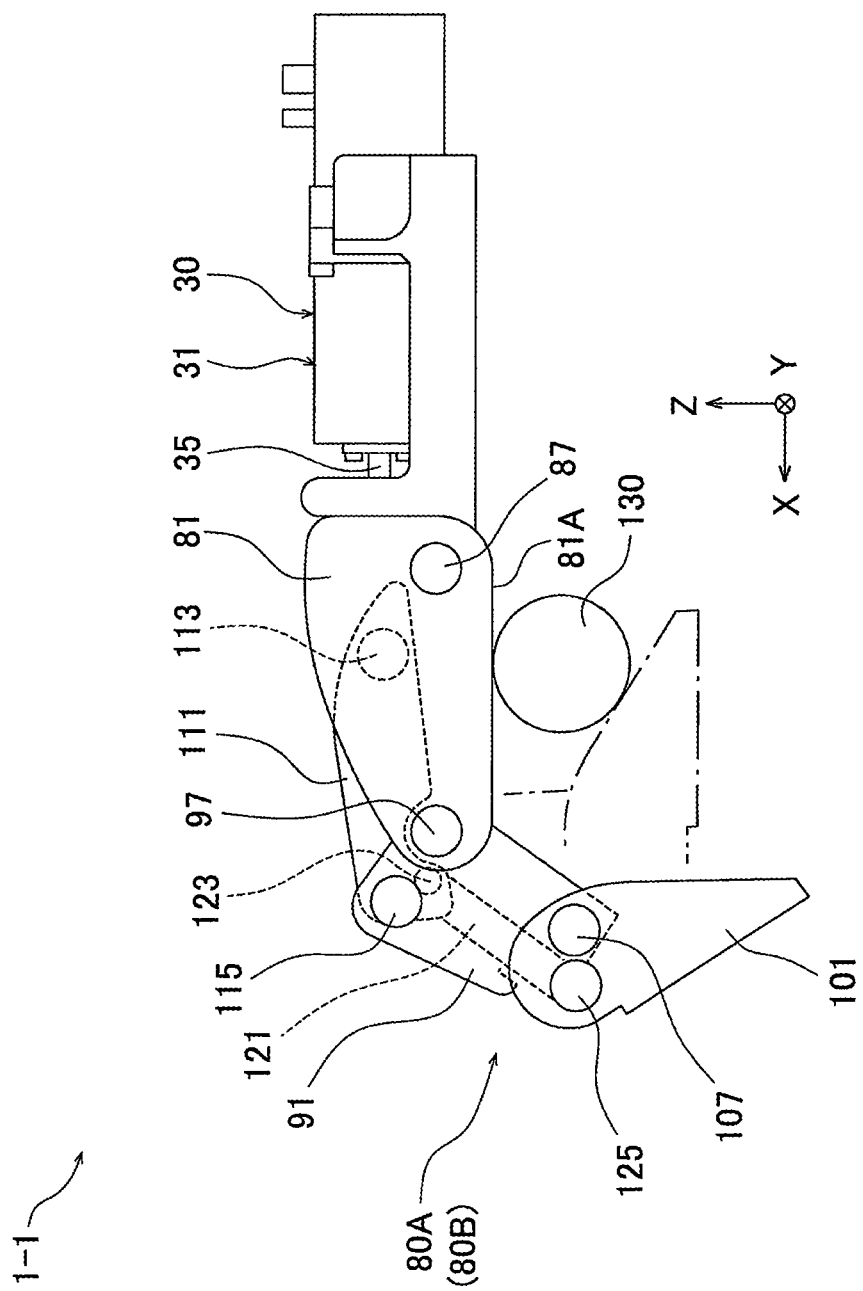
FIG. 5 is an illustration for explaining movement of the hand 1-1.
Figure 6:
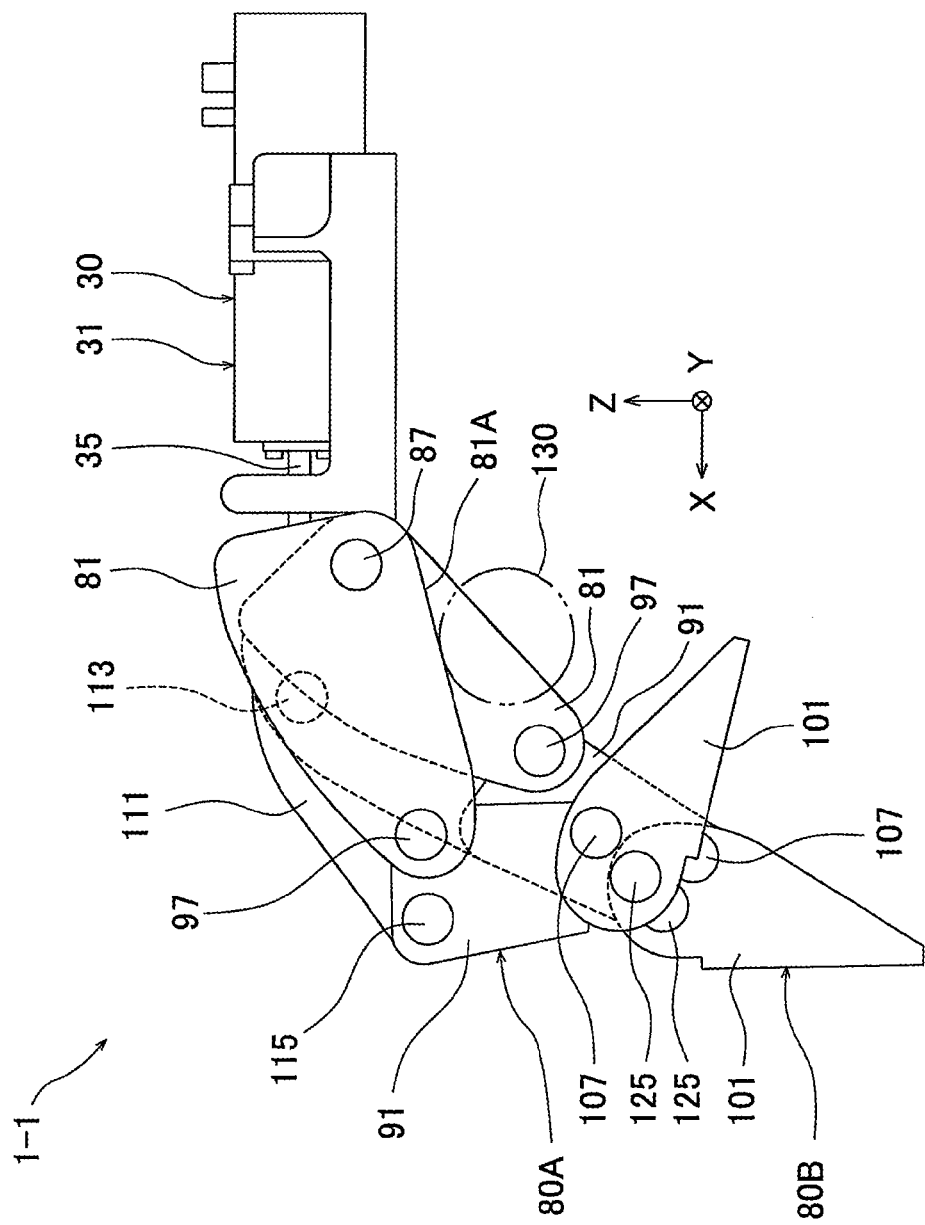
FIG. 6 is an illustration for explaining movement of the hand 1-1.

Now, movement of the hand 1-1 as described above will be explained. FIG. 4 through FIG. 6 are illustrations for explaining movement of the hand 1-1. In a state that the rod 35 of the linear actuator 31 is maximally retracted into the actuator body 33 as shown in FIG. 2, the slide member 41 and the third connecting part 113 are located nearest to the actuator body 33 and the first, second, and third digital parts 81, 91, 101 are held to align substantially horizontally.

As the linear actuator 31 is driven from the aforementioned state so that the slide member 41 is pushed forward (in the direction of arrow X) via the rod 35, the third connecting part 113 is extruded toward the fourth connecting part 115 so that the first, second, and third digital parts 81, 91, 101 are rotated integrally about the first connecting part 87 as shown in FIG. 4 by means of moment about the first connecting part 87. The reason why the first, second, and third digital parts 81, 91, 101 are rotated integrally is that biasing force is applied to keep the alignment of the first, second, third digital parts 81, 91, 101 linear as a whole. As the rod 35 is further extruded forward, as shown by dashed lines in FIG. 4, the first, second and third digital parts 81, 91, 101 are further rotated while keeping their alignment. For example, this movement is used for pinching something with fingertips. On the other hand, as the linear actuator 31 is driven to retract the slide member 41, the first, second, and third digital parts 81, 91, 101 move inversely to the aforementioned movement and are thus rotated together in the opposite direction while keeping their alignment so that they return to the state shown in FIG. 2.

As shown in FIG. 5, there is an object 130 being in contact with a lower surface 81A on a moving side (grasping side, inside) of the first digital part 81. As the linear actuator 31 is driven from the aforementioned state so that the slide member 41 is pushed forward (in the direction of arrow X) via the rod 35, the third connecting part 113 is extruded toward the fourth connecting part 115. Since the first digital part 81 is prevented from rotating by the object 130, the force pushing the third connecting part 113 overcomes the biasing force of the biasing means (biasing force for keeping the alignment of the first, second, third digital parts 81, 91, 101 linear), whereby the second digital part 91 rotates about the second connecting part 97. Since the sixth connecting part 123 disposed on the first driving part 111 is displaced forward relative to the fourth connecting part 115, the second driving part 121 is pushed forward. Accordingly, the seventh connecting part 125 is pushed forward so that the third digital part 101 rotates about the fifth connecting part 107 downward relative to the second digital part 91.

As the linear actuator 31 is further driven so that the slide member 41 is further pushed forward via the rod 35, the second digital part 91 and the third digital part 101 are further flexed while the first digital part 81 remains stationary, thereby grasping the object 130 as shown by dashed lines or imaginary lines in FIG. 5.

As the linear actuator 31 is driven from the state shown in FIG. 5 to retract the slide member 41, the second and third digital parts 91, 101 move inversely to the aforementioned movement and are thus rotated about the second and fifth connecting parts 97, 107 in the opposite direction so that they return to the state shown in FIG. 2.

With regard to FIG. 5, description was made with regard to a case that the object 130 is in contact with the first digital part 81 when the first digital part 81 extends horizontally so that the first digital part 81 is prevented from rotating from the horizontally extending state. On the other hand, also in case that the first digital part 81 comes in contact with an object so as to stop after rotating at a predetermined angle from the horizontally extending state as shown in FIG. 4, the second and third digital parts 91, 101 are flexed relative to the first digital part 81 after the position where the first digital part 81 stops.

As apparent from the above description, in the hand 1-1, the first driving part 111 is connected to the second digital part 91 by the fourth connecting part 115 and the first digital part 81 is connected to the second digital part 91 by the second connecting part 97 located on the inside of the fourth connecting part 115, whereby the driving force of the first driving part 111 connected to the driving mechanism 30 is first transferred to the second digital part 91 and then transferred to the first digital part 81 to apply torque about the first and second connecting parts 87, 97 to the first and second digital parts 81, 91.

With regard to FIG. 4 and FIG. 5, description was made as regard to a case that the pair of fingers 80A, 80B of the hand 1-1 provide the same movement. On the other hand, the fingers 80A, 80B of the hand 1-1 can provide different movements from each other. That is, as shown in FIG. 6, the lower surface 81A of the first digital part 81 of the one finger 80A comes in contact with the object 130 at a position where the first digital part 81 rotates a little from the horizontally extending position while the other finger 80B never come in contact with the object 130. Such situation is typical according to the configuration of an object 130.

As the linear actuator 31 is driven from the state shown in FIG. 2 so that the slide member 41 is pushed forward (in the direction of arrow X) via the rod 35, the fingers 80A and 80B conduct the same movement as mentioned above until the first digital part 81 of the finger 80A comes in contact with the object 130 in FIG. 6. That is, the fingers 80A and 80B rotate about the first connecting part 87 while keeping their alignment linear. As the slide member 41 is further pushed forward, in the finger 80A being in contact with the object 130, the first digital part 81 stays in the position and the second digital part 91 and the third digital part 101 are flexed. On the other hand, the finger 80B not being in contact with the object 130 rotates about the first connecting part 87 while keeping the alignment linear. Of course, if the first digital part 81 of the finger 80B comes in contact with the object 130 during the rotation of the finger 80B, at the position, the first digital part 81 stops and the second and third digital parts 91, 101 start to be flexed. It should be noted that, even though the fingers 80A and 80B are flexed differently from each other, the third connecting parts 113 of the fingers 80A and 80B are positioned at the same level.

That is, the hand 1-1 is composed of the two fingers 80A and 80B which are arranged in parallel in which, by pushing the third connecting part 113 toward the fourth connecting part 115, the first digital part 81, the second digital part 91, and the third digital part 101 are rotated together about the first connecting part 87 or when the first digital part 81 is blocked from rotation, the second and third digital parts 91, 101 rotate about the second and fifth connecting parts 97, 107. The single driving mechanism 30 which drives the third connecting parts 113 of the respective fingers 80A and 80B linearly for the same distance and in the same direction makes it possible to drive the two fingers 80A and 80B at a time.

As mentioned above, according to the hand 1-1, the fingers 80A and 80B arranged in parallel are driven by the single driving mechanism 30 at a time, thereby easily flexing the first, second, and third digital parts 81, 91, 101 of the respective fingers 80A and 80B into different shapes according to the configuration of the object 130 to be grasped. This makes the movement similar to the movement of a plurality of fingers of a human hand easy.

Since only the single driving mechanism 30 is employed which drives the third connecting parts 113 of the respective fingers 80A and 80B for the same distance and in the same direction, it allows simple structure and also reduction in size, cost, and weight. In addition, since the driving mechanism 30 is composed of the linkage member 40 rotatably connected to the third connecting part 113 to linearly and reciprocatably move the third connecting part 113 and the linear actuator 31 for moving the linkage member 40, the structure is quite simple.

Second Embodiment

Figure 7:
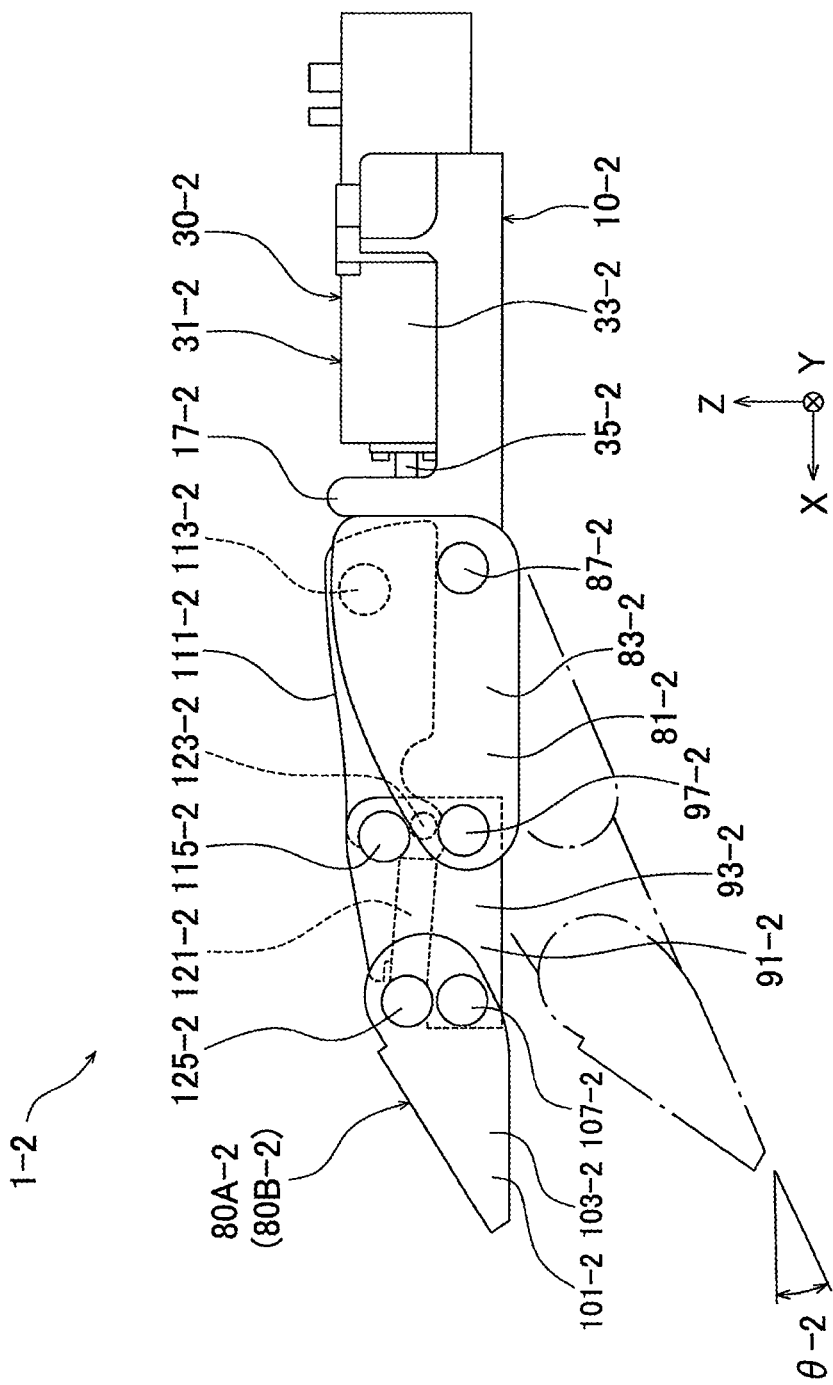
FIG. 7 is a side view of a hand 1-2.

FIG. 7 is a side view of a hand 1-2 to which an articulated mechanism according to the second embodiment of the present invention is applied. In the hand 1-2 shown in FIG. 7, parts identical or corresponding to the parts of the hand 1-1 shown in FIG. 1 through FIG. 6 are marked with the same reference numerals (but the suffix "-2" is added to the respective reference numerals). Items other than items as will be described below are the same as those of the hand 1-1 shown in FIG. 1 through FIG. 6. Points of the hand 1-2 different from the hand 1-1 are a point that the position of the third connecting part 113-2 is changed and a point that the shape of the first driving part 111-2 is changed according to the change of the third connecting part 113-2.

That is, the position of the third connecting part 113-2 of the hand 1-2 is higher than the position of the third connecting part 113 of the hand 1-1 shown in FIG. 2. According to this structure, when the third connecting part 113-2 shown in FIG. 7 is linearly moved toward the fourth connecting part 115-2 for a distance equal to the distance for linearly moving the third connecting part 113 toward the fourth connecting part 115 such that the finger 80A rotates to the position shown by solid lines in FIG. 4, the finger 80A-2 rotates to a position shown by dashed lines in FIG. 7. The rotation angle [θ-2] of the finger 80A-2 for this movement is smaller than the rotation angle [θ] of the aforementioned finger 80A (see FIG. 4) (i.e. [θ-2]<[θ]).

That is, by changing the position of the third connecting part 113-2 from the position of the third connecting part 113, the rotation angle [θ-2] of the finger 80A-2 is made different from the rotation angle [θ] of the finger 80A. The effect is true for a case of changing the position of the first connecting part 87-2, the second connecting part 97-2, or the fourth connecting part 115-2. Further, the effect is true for a case of changing the positions of a plurality of connecting parts.

Therefore, in case of employing the finger 80A (or 80B) shown in FIG. 1 through FIG. 6 as one of fingers and employing the finger 80A-2 (or 80B-2) shown in FIG. 7 as the other finger, the respective fingers can be flexed differently from each other by driving the third connecting parts 113 (113-2) for the same distance and in the same direction at a time with the single driving mechanism 30 (30-2) even though the fingers are not in contact with an object. For example, when a human hand grasps an object, generally the fifth finger is flexed first and other fingers follow. Such movement is achieved by the simple structure.

Third Embodiment

Figure 8:
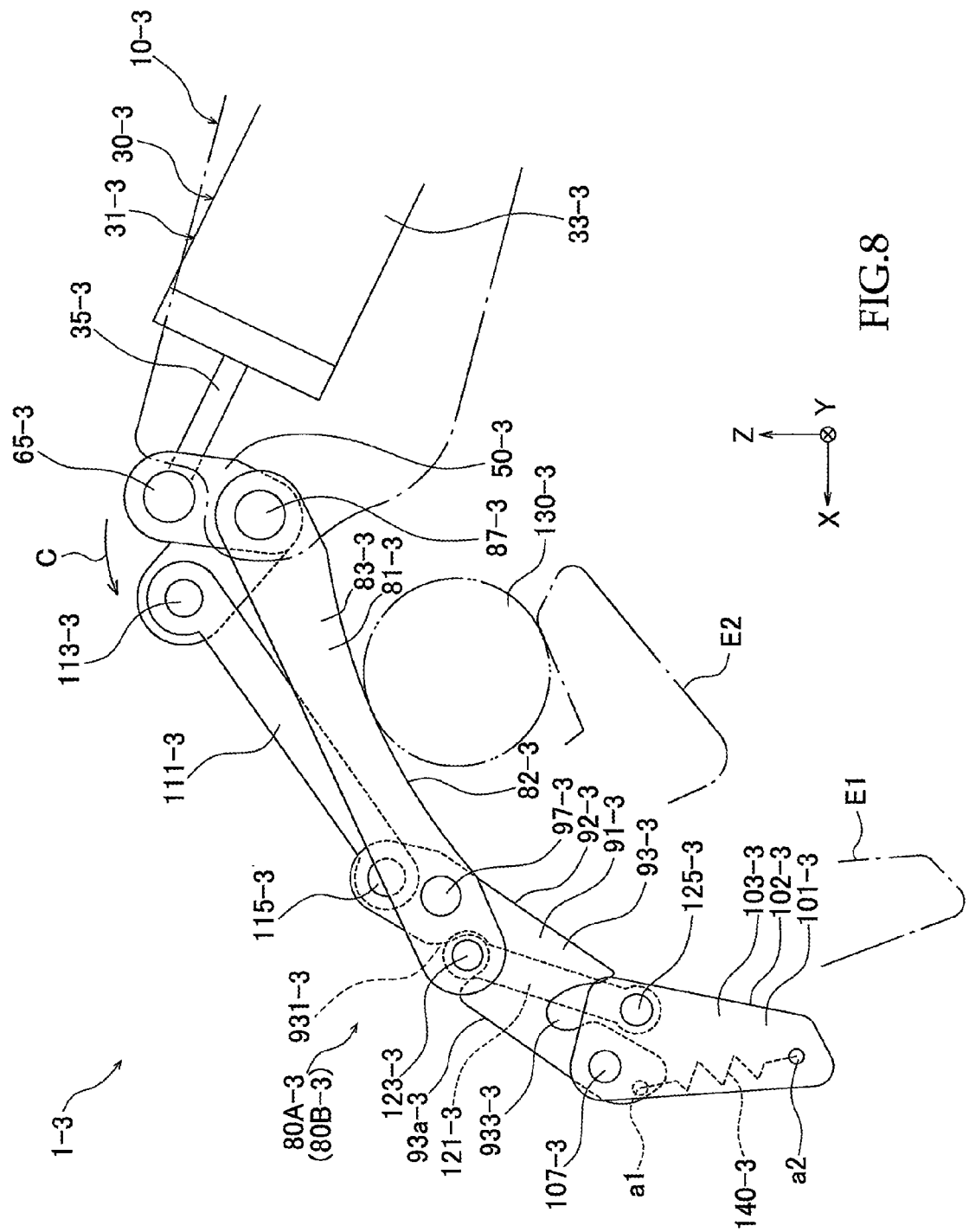
FIG. 8 is a side view of a hand 1-3.
Figure 9:
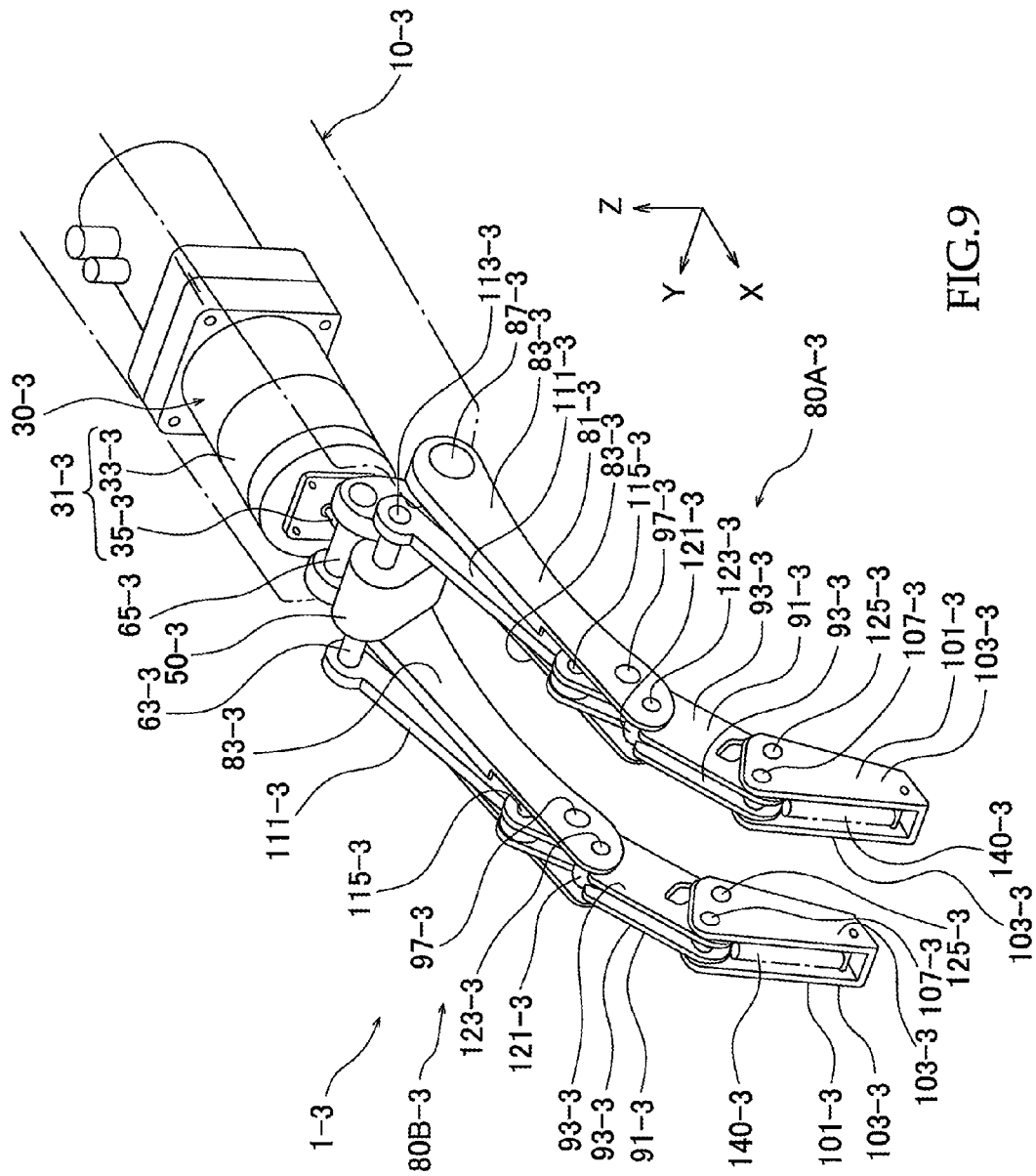
FIG. 9 is a perspective view of the hand 1-3 as seen from obliquely above.
Figure 10:
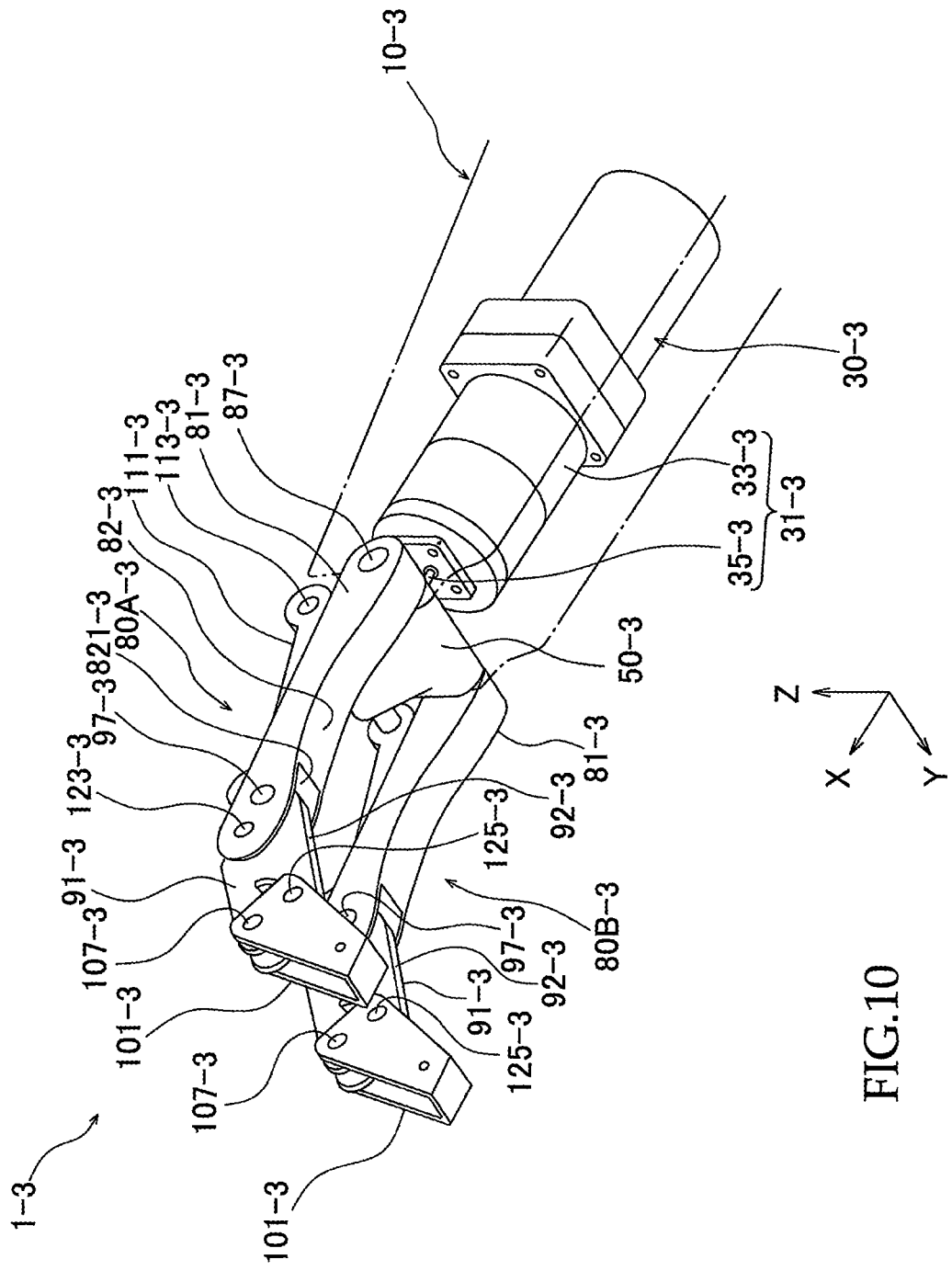
FIG. 10 is a perspective view of the hand 1-3 as seen from obliquely below.

FIG. 8 is a side view of a hand 1-3 to which an articulated mechanism according to the third embodiment of the present invention is applied, FIG. 9 is a perspective view of the hand 1-3 as seen from obliquely above, and FIG. 10 is a perspective view of the hand 1-3 as seen from obliquely below. In the hand 1-3 shown in FIG. 8 through FIG. 10, parts identical or corresponding to the parts of the hand 1-1 shown in FIG. 1 through FIG. 6 are marked with the same reference numerals (but the suffix "-3" is added to the respective reference numerals). Items other than items as will be described below are the same as those of the hand 1-1 shown in FIG. 1 through FIG. 6. As shown in these figures, the hand 1-3 comprises a mounting member 10-3, a driving mechanism 30-3 mounted to the mounting member 10-3, and a pair of fingers 80A-3, 80B-3 attached to the mounting member 10-3 and to be driven by the driving mechanism 30-3.

The mounting member 10-3 is shown by dashed lines or imaginary lines. A linear actuator 31-3 of the driving mechanism 30-3 is attached to the mounting member 10-3, and the mounting member 10-3 supports a linkage member 50-3 and a first digital part 81-3 at a first connecting part 87-3 such that the linkage member 50-3 and the first digital part 81-3 can rotate independently.

The driving mechanism 30-3 comprises the linear actuator 31-3 and the linkage member 50-3. The structure of the linear actuator 31-3 is the same as the structure of the aforementioned linear actuator 31.

Figure 11:
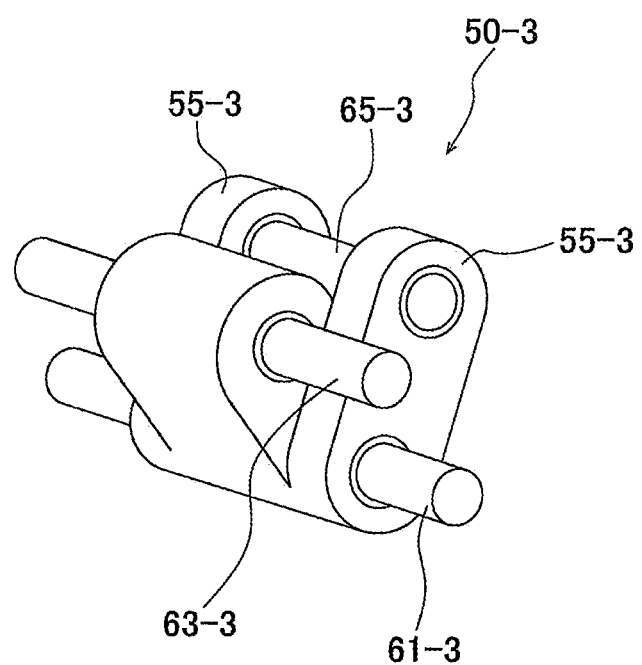
FIG. 11 is a perspective view of a connecting member 50-3.

FIG. 11 is a perspective view of the linkage member 50-3. As shown in this drawing, the linkage member 50-3 is in a block configuration having a generally heart shape as seen from the side. The linkage member 50-3 has a first connecting part shaft 61-3 rotatably inserted into a bore formed in a lower central portion of the linkage member 50-3, a third connecting part shaft 63-3 rotatably inserted into a bore formed in an upper portion of one of biforked portions of the linkage member 50-3, and further a connecting rod 65-3 rotatably disposed between a pair of side walls 55-3 of upper portions of the other biforked portions of the linkage member 50-3.

The both end portions of the first connecting part shaft 61-3 of the linkage member 50-3 are attached to the mounting member 10-3. The first connecting part 87-3 of the first digital part 81-3 is rotatably disposed on the both ends of the first connecting part shaft 61-3 projecting outside of the mounting member 10-3 after the penetration. That is, the linkage member 50-3 and the first digital part 81-3 are attached to the mounting member 10-3 such that they are rotatable independently from each other.

At a middle portion of the connecting rod 65-3 of the linkage member 50-3, an end of a rod 35-3 of the linear actuator 31-3 is attached. The both ends of the third connecting shaft 63-3 of the linkage member 50-3 are attached to the third connecting part 113-3 of the first driving part 111-3. As apparent from the above, the linkage member 50-3 is arranged such that the first connecting part 87-3 and the third connecting part 113-3 and the linkage rod 65-3 become corners of a triangular shape as seen from the side of the linkage member 50-3 to link the linear actuator 31-3 and the two fingers 80A-3 and 80B-3.

Since the fingers 80A-3 and 80B-3 have the same structure, description will be made mainly as regard to one of the fingers 80A-3. The finger 80A-3 comprises the first digital part 81-3 rotatably connected to the mounting member 10-3 by the first connecting part 87-3 on the proximal side (the side near the mounting member 10-3), a second digital part 91-3 of which proximal side is rotatably connected to the distal side of the first digital part 81-3 (the side away from the mounting member 10-3) by a second connecting part 97-3, a third digital part 101-3 of which proximal side is rotatably connected to the distal side of the second digital part 91-3 by a fifth connecting part 107-3, and a first driving part 111-3 of which distal side is rotatably connected to a proximal side of the second digital part 91-3 by a fourth connecting part 115-3 and of which proximal side is connected to the third connecting part 113-3 for applying driving force, and a second driving part 121-3 of which distal side is rotatably connected to a seventh connecting part 125-3 at the proximal side of the third digital part 101-3 and of which proximal side is rotatably connected to a sixth connecting part 123-3 at the distal side of the first digital part 81-3.

Figure 12A:
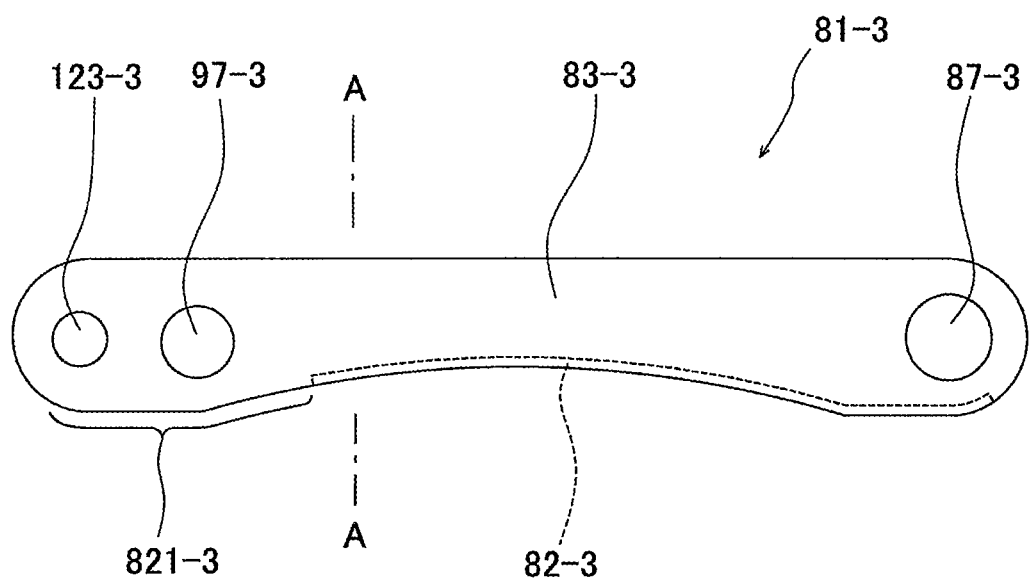
FIG. 12(*a*) is a side view of a first digital part 81-3 and FIG. 12(*b*) is a sectional view of FIG. 12(*a*) with respect to a line A-A
Figure 12B:
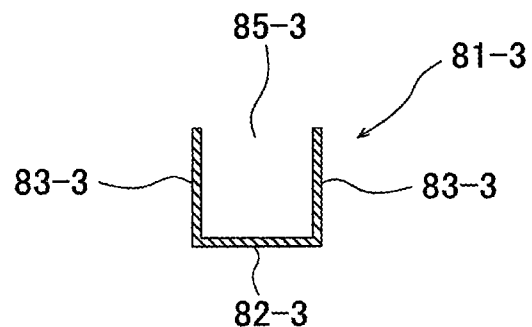

FIGS. 12(a), 12(b) show the first digital part 81-3 in which FIG. 12(a) is a side view thereof, FIG. 12(b) is a sectional view taken along a line A-A of FIG. 12(a). As shown in FIGS. 12(a), 12(b) and FIG. 8 through FIG. 10, the first digital part 81-3 is made of a plate (board) and is formed in a U-like shape so as to form a pair of side wall portions 83-3, 83-3 extending parallel from the both sides of a lower surface of a bottom 82-3. At the proximal portions of the side wall portions 83-3, 83-3, the first connecting part 87-3 is arranged as mentioned above. By the first connecting part 87-3, the first digital part 81-3 is rotatably connected to the mounting member 10-3. The first digital part 81-3 is arranged such that the lower surface of the bottom 82-3 faces to the inside (the palm side) and accordingly an opening 85-3 opens on the outer side (back side). The first connecting part 87-3 is provided with a bearing. At the distal side of the first digital part 81-3, the second connecting part 97-3 is disposed. At a portion between the second connecting part 97-3 and the distal end of the first digital part 81-3, the sixth connecting part 123-3 is disposed. The first digital part 81-3 is provided with an insertion opening 821-3 which is formed by cutting out the bottom portion 82-3 from a position below about the second connecting part 97-3 to the distal end thereof.

Figure 13:
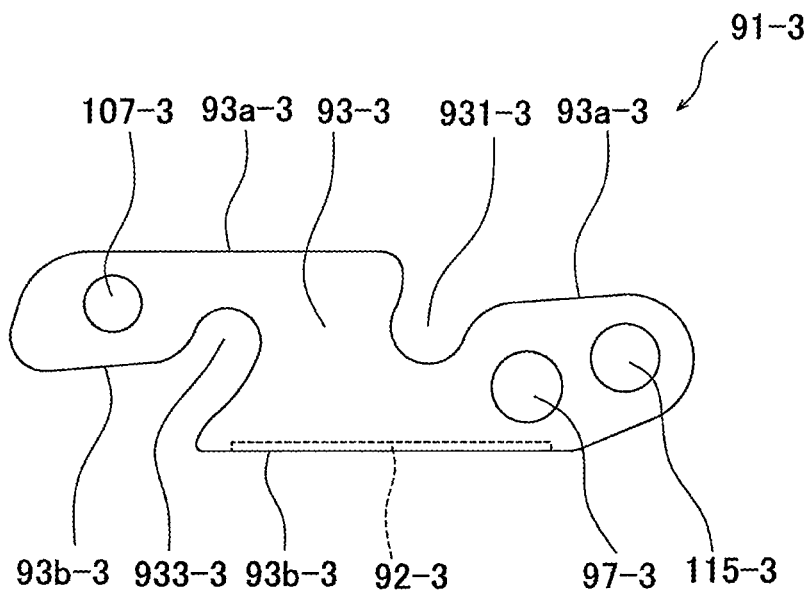
FIG. 13 is a side view of a second digital part 91-3.

FIG. 13 is a side view of the second digital part 91-3. As shown in FIG. 13 and FIG. 8 through FIG. 10, the second digital part 91-3 is made of a plate (board) and is formed in a U-like shape so as to form a pair of side wall portions 93-3, 93-3 extending parallel from the both sides of a lower surface of a bottom 92-3. At the proximal portions of the side wall portions 93-3, 93-3, the second connecting part 97-3 is disposed. By the second connecting part 97-3, the second digital part 91-3 is rotatably connected to the side wall portions 83-3, 83-3 of the first digital part 81-3. At the second connecting part 97-3, a shaft is provided between the side wall portions 83-3, 83-3 (93-3, 93-3) (the same is true for the other connecting parts). The both side wall portions 93-3 of the second digital part 91-3 each have a portion projecting over the second connecting part 97-3 to the proximal end, where the fourth connecting part 115-3 rotatably attached to the first driving part 111-3 is disposed. The side wall portions 93-3 of the second digital part 91-3 each have a substantially U-like sixth connecting part cutout 931-3 formed in each back-side edge 93a-3 at a position on the distal side from the second connecting part 97-3. In the sixth connecting part cutout 931-3, the sixth connecting part 123-3 is inserted. On the side of the back-side edge 93a-3, a portion from the sixth connecting part cutout 931-3 to the proximal end is lower than the other portion from the sixth connecting part cutout 931-3 to the distal end. The side wall portions 93-3 of the second digital part 91-3 each have a substantially U-like seventh connecting part cutout 933-3 formed in each inside (palm-side) edge 93b-3 at a position on the proximal side from the fifth connecting part 107-3. In the seventh connecting part cutout 933-3, the seventh connecting part 125-3 is inserted. On the side of the inside edge 93b-3, a portion from the seventh connecting part cutout 933-3 to the distal end is higher than the other portion from the seventh connecting part cutout 933-3 to the proximal end. The width dimension between the outer surfaces of the side wall portions 93-3 of the second digital part 91-3 is set to be slightly smaller than the width dimension between the inner surfaces of the side wall portions 83-3 of the first digital part 81-3. For connecting the second digital part 91-3 and the first digital part 81-3 at the second connecting part 97-3, accordingly, a proximal-side portion of the second digital part 91-3 is inserted into the space between the right and left side wall portions 83-3 of a distal-side portion of the first digital part 81-3. In this regard, the sixth connecting part cutout 931-3 is arranged between the side wall portions 83-3 of the first digital part 81-3. The proximal-side portion of the second digital part 91-3 is fitted into the insertion opening 821-3 of the first digital part 81-3. The second digital part 91-3 is arranged such that the lower surface of the bottom 92-3 faces to the palm side.

Figure 14:
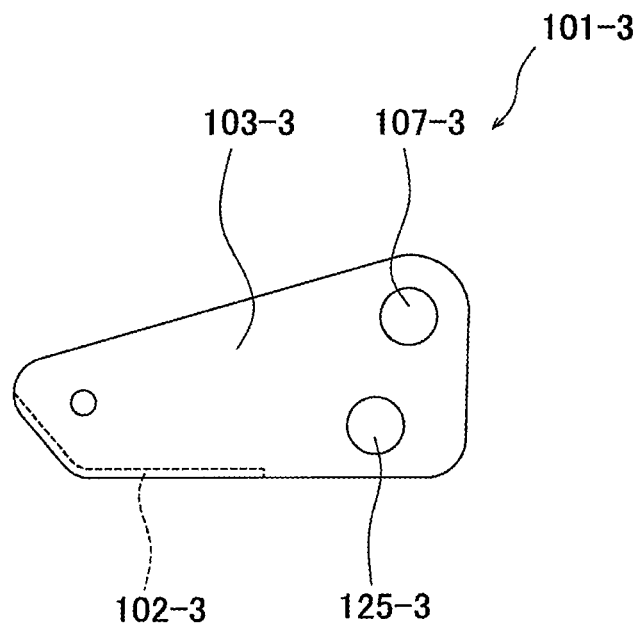
FIG. 14 is a side view of a third digital part 101-3.

FIG. 14 is a side view of the third digital part 101-3. As shown in FIG. 14 and FIG. 8 through FIG. 10, the third digital part 101-3 is made of a plate (board) and is formed in a U-like shape so as to form a pair of side wall portions 103-3, 103-3 extending parallel from the both sides of a lower surface of a bottom 102-3. At the upper portions of the proximal portions of the side wall portions 103-3, 103-3, the fifth connecting part 107-3 is disposed. By the fifth connecting part 107-3, the third digital part 101-3 is rotatably connected to the second digital part 91-3. The seventh connecting part 125-3 is disposed below the fifth connecting part 107-3.

As shown in FIG. 8 through FIG. 10, the first driving part 111-3 is a bar-like plate and is rotatably connected to the linkage member 50-3 by the third connecting part 113-3 at the proximal side thereof as mentioned above. On the other hand, the first driving part 111-3 is rotatably connected to a portion between the second connecting part 97-3 and the proximal end of the second digital part 91-3 by the fourth connecting part 115-3 at the distal side of the first driving part 111-3. That is, the first driving part 111-3 is connected to the second digital part 91-3 by the fourth connecting part 115-3, while the first digital part 81-3 is connected to the second digital part 91-3 by the second connecting part 97-3 on the inside of the fourth connecting part 115-3. Further, the fourth connecting part 115-3 is partly inserted into the opening 85-3 formed on the outside (back-side) of the first digital part 81-3.

The second driving part 121-3 is a bar-like plate similar to the first driving part 111-3 and is rotatably connected to a portion between the second connecting part 97-3 and the distal end of the first digital part 81-3 by the sixth connecting part 123-3 at the proximal side of the driving part 121-3. On the other hand, the driving part 121-3 is rotatably connected to a proximal end portion (on the inside of the fifth connecting part 107-3) of the third digital part 101-3 by the seventh connecting part 125-3 at the distal side of the driving part 121-3.

Between the second digital part 91-3 and the third digital part 101-3, a biasing means 140-3 composed of a tension spring is arranged to always apply biasing force in such a direction that the second and third digital parts 91-3 and 101-3 are broadened (the third digital part 101-3 is rotated about the fifth connecting part 107-3 toward the outside (back-side) relative to the second digital part 91-3). It should be noted that the fifth connecting part 107-3 is positioned on the inside (palm side) of a supporting point a1 of the biasing means 140-3 on the second digital part 91-3. In other words, the biasing means 140-3 biases to shorten the distance between the supporting point a1 fixed to the second digital part 91-3 and a supporting point a2 fixed to the third digital part 101-3. When the third digital part 101-3 is rotated toward inside (palm side) relative to the second digital part 91-3, the distance between the both supporting points a1, a2 becomes longer so that they are biased to return to the original positions. Therefore, the first and second digital parts 81-3 and 91-3 are also biased in a broadening direction. As a result of this, the first, second, and third digital parts 81-3, 91-3 and 101-3 are all biased in the broadening direction. Instead of the position mentioned above, the biasing means 140-3 may be mounted between the first and second digital parts 81-3, 91-3 to apply biasing force in such a direction that the first and second digital parts 81-3 and 91-3 are always broadened.

Now, movement of the hand 1-3 as described above will be explained. FIG. 8 illustrates a state where the rod 35-3 of the linear actuator 31-3 is maximally retracted into the actuator body 33-3. In this state, the linkage member 50-3 is maximally rotated rightward (in a direction opposite to the direction of arrow C) about the first connecting part 87-3. At this point, the fingers 80A-3 and 80B-3 open.

From the aforementioned state, the linear actuator 31-3 is driven to extrude the rod 35-3 thereof. If there is no object 130-3 shown in FIG. 8 at this point, the linkage member 50-3 rotates leftward (in the direction of arrow C) about the first connecting part 87-3 so that the third connecting part 113-3 is extruded toward the fourth connecting part 115-3. Accordingly, the first, second, and third digital parts 81-3, 91-3, 101-3 are rotated integrally about the first connecting part 87-3 (as shown by dashed lines E1 of FIG. 8). The reason why the first, second, and third digital parts 81-3, 91-3, 101-3 are rotated integrally is because the biasing means 140-3 applies biasing force keeping the first, second, and third digital parts 81-3, 91-3, and 101-3 in the opening state as a whole. This movement is used for pinching something with fingertips. On the other hand, as the linear actuator 31-3 is driven to retract the rod 35-3 extruded, the first, second, and third digital parts 81-3, 91-3, 101-3 move inversely to the aforementioned movement and are thus rotated together in the opposite direction about the first connecting part 87-3 while keeping their alignment so that they return to the state shown in FIG. 8.

Figure 15:
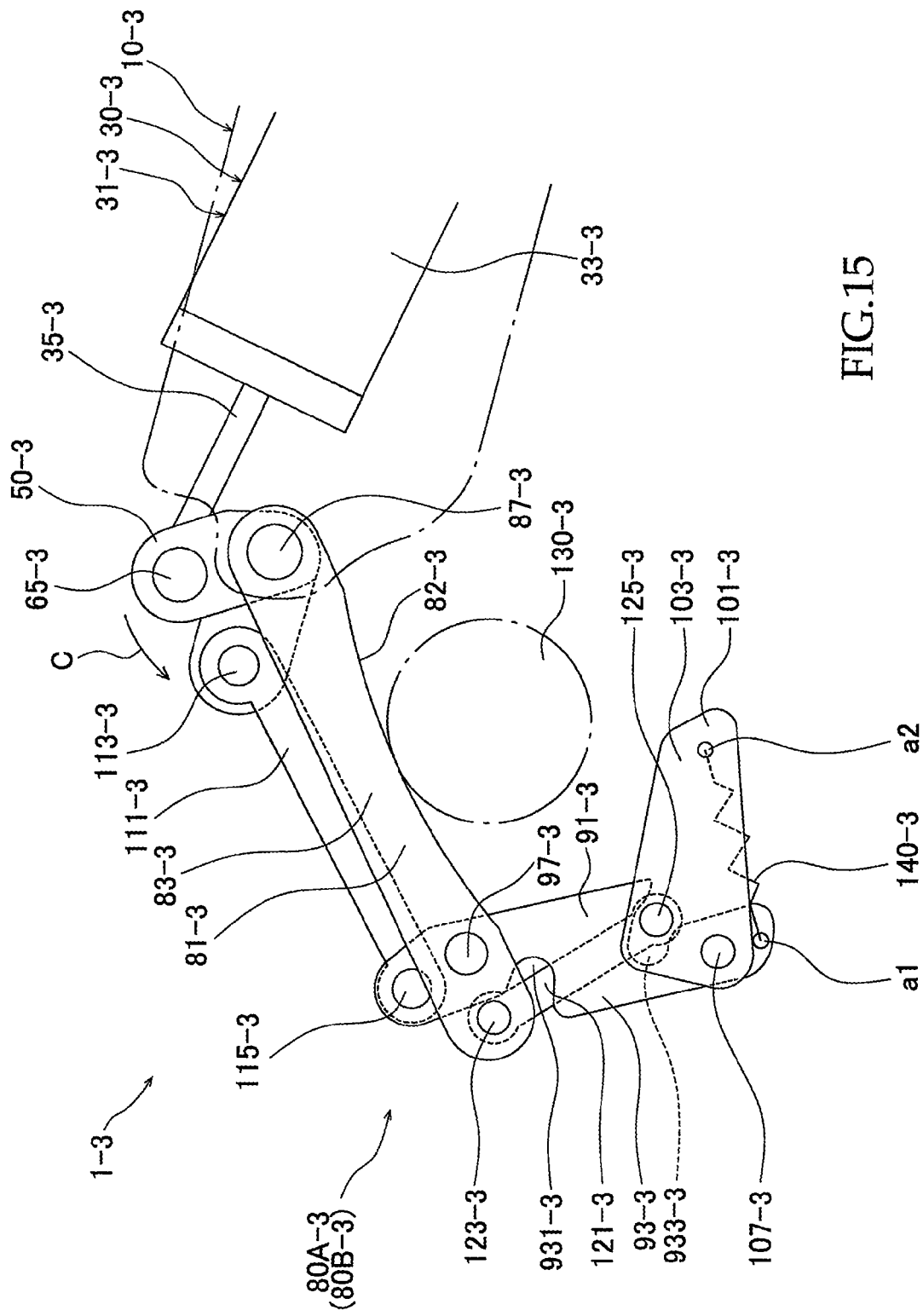
FIG. 15 is an illustration for explaining movement of the hand 1-3.

Now, description will be made on assumption that an object 130-3 is in contact with the lower surface 82-3 on a moving side (grasping side, inside) of the first digital part 81-3. As the linear actuator 31-3 is driven from the aforementioned state so that the linkage member 50-3 is rotated about the first connecting part 87-3 leftward via the rod 35-3, the third connecting part 113-3 is extruded toward the fourth connecting part 115-3. Since the first digital part 81-3 is prevented from rotating by the object 130-3, the force pushing the third connecting part 113-3 overcomes the biasing force of the biasing means 140-3, whereby the second digital part 91-3 rotates about the second connecting part 97-3 as shown in FIG. 15. Though the sixth connecting part 123-3 disposed on the first digital part 81-3 remains stationary, the sixth connecting part 123-3 is relatively displaced (retracted) with respect to the fourth connecting part 115-3 toward the fourth connecting part 115-3 because the fourth connecting part 115-3 moves due to the rotation of the second digital part 91-3 about the second driving part 97-3. Accordingly, the second driving part 121-3 is retracted rearward with respect to the second digital part 91-3 so that the sixth connecting part 123-3 moves in a direction of getting out of the sixth connecting part cutout 931-3. Thus, the seventh connecting part 125-3 is retracted rearward and enters into the seventh connecting part cutout 933-3 so that the third digital part 101-3 rotates inwardly about the fifth connecting part 107-3 relative to the second digital part 91-3. When the second digital part 91-3 is flexed inwardly relative to the first digital part 81-3, the fourth connecting part 115-3 is exposed outside of the opening 85-3 of the first digital part 81-3 as shown in FIG. 15.

Therefore, the second digital part 91-3 and the third digital part 101-3 are flexed, thereby grasping the object 130-3 finally (as shown by dashed lines E2 of FIG. 8). In other words, since the second driving part 121-3 is connected to the distal end portion of the first digital part 81-3 by the sixth connecting part 123-3 and the second digital part 91-3 is connected to the first digital part 81-3 by the second connecting part 97-3 on the inside of the sixth connecting part 123-3, the second driving part 121-3 pulls the third digital part 101-3 at the seventh connecting part 125-3 on the inside of the fifth connecting part 107-3 when the second digital part 91-3 is rotated relative to the first digital part 81-3. Accordingly, the second digital part 91-3 and the third digital part 101-3 are concurrently rotated inwardly and are thus flexed to grasp the object 130-3. That is, when the second digital part 91-3 is rotated relative to the first digital part 81-3, the third digital part 101-3 is always rotated relative to the second digital part 91-3. By the way, any of the first digital part 81-3, the second digital part 91-3, and the third digital part 101-3 is formed by bending a plate into a U-like shape of which lower surface 82-3, 92-3, 102-3 of a bottom is arranged to face to the inside. Therefore, these lower surfaces 82-3, 92-3, and 102-3 can function as contact surfaces to the object 130-3 directly. Accordingly, additional part functioning as the contact surface is no longer required, thus simplifying the structure and reducing the weight.

As the linear actuator 31-3 is driven to rotate the linkage member 50-3 rightward about the first connecting part 87-3, the second and third digital parts 91-3, 101-3 move inversely to the aforementioned movement and are thus rotated about the second and fifth connecting parts 97-3, 107-3 in the opposite direction so that they return to the state shown by solid lines in FIG. 8. That is, for grasping the object, rotation starts with the first digital part 81-3, while for releasing the object, rotation starts with the side of the biasing means 140-3 (the sides of the second, third digital parts 91-3, 101-3) i.e. the opposite side.

Also in case that the first digital part 81-3 comes in contact with an object 130-3 so as to stop after rotating at a predetermined angle from the state as shown in FIG. 8, the second and third digital parts 91-3, 101-3 are flexed relative to the first digital part 81-3 after the position where the first digital part 81-3 stops, similarly to the case of the aforementioned hand 1-1.

As in the hand 1-3, the first driving part 111-3 is connected to the second digital part 91-3 by the fourth connecting part 115-3 and the first digital part 81-3 is connected to the second digital part 91-3 by the second connecting part 97-3 located on the inside of the fourth connecting part 115-3, whereby the driving force of the first driving part 111-3 connected to the driving mechanism 30-3 is first transferred to the second digital part 91-3 and then transferred to the first digital part 81-3 to apply torque about the first and second connecting parts 87-3, 97-3 to the first and second digital parts 81-3, 91-3.

By the way, in the hand 1-3, since the fourth connecting part 115-3 is disposed on a portion between the second connecting part 97-3 and the proximal end of the second digital part 91-3 as shown in FIG. 8, the second and fourth connecting parts 97-3, 115-3 do not overlap each other in the vertical direction, thereby allowing reduction in height size of a portion around the second connecting part 97-3 connecting the first and second digital parts 81-3, 91-3. At the same time, a part of the fourth connecting part 115-3 enters into the opening 85-3, opening on the outer side, of the first digital part 81-3 so that a space inside the first digital part 81-3 is utilized as a part of the space for pivotal movement of the fourth connecting part 115-3, thereby reducing the projecting amount (projecting dimension) of the fourth connecting part 115-3 projecting outwardly from the opening 85-3 of the first digital part 81-3 when the second digital part 91-3 is flexed inwardly relative to the first digital part 81-3. That is, even though the first and second digital parts 81-3 and 91-3 take any position (opened or closed), this structure allows reduction in height size of the portion around the second connecting part 97-3 connecting the first and second digital parts 81-3 and 91-3.

On the other hand, since there is a sixth connecting part 123-3 on the portion between the second connecting part 97-3 and the distal end, the second and sixth connecting parts 97-3 and 123-3 do not overlap each other in the vertical direction. The sixth connecting part 123-3 is disposed on the first digital part 81-3 in order to connect the second driving part 121-3 for driving the third digital part 101-3. This structure also allows reduction in height size of the portion around the second connecting part 97-3 connecting the first and second digital parts 81-3, 91-3. In addition, the sixth connecting part cutout 931-3 formed in the second digital part 91-3 is disposed between the right and left side wall portions 83-3 of the first digital part 81-3, thereby reducing the projecting amount (projecting dimension) of the sixth connecting part 123-3 projecting outwardly from the second digital part 91-3. That is, even though the first and second digital parts 81-3 and 91-3 take any position (opened or closed), this structure also allows reduction in height size of the portion around the second connecting part 97-3 connecting the first and second digital parts 81-3 and 91-3.

Further, since any of the first and second driving parts 111-3, 121-3 is a bar-like plate, a small width distance between the side wall portions 93-3 is enough even though the first and second driving parts 111-3, 121-3 enter into the space between the both side wall portions 93-3 of the second digital part 91-3. Accordingly, the width distance of the second digital part 91-3 can be minimized.

By the way, in the hand 1-3, when the position where the object 130-3 comes in contact with the first digital part 81-3 of the finger 80A is different from the position where the object 130-3 comes in contact with the first digital part 81-3 of the other finger 80B-3, the positions of the respective third connecting parts 113-3 are fixed while the respective fingers 80A-3, 80B-3 move differently from each other, similarly to the hand 1-1. That is, also in the hand 1-3, the fingers 80A-3 and 80B-3 arranged in parallel are driven by the single driving mechanism 30-3 at a time, whereby the first, second, and third digital parts 81-3, 91-3, 101-3 of the respective fingers 80A-3 and 80B-3 can be easily flexed differently according to the configuration of the object 130-3 to be grasped. This makes the movement similar to the movement of a plurality of fingers of a human hand easy.

Also in the hand 1-3, if the position of any of the first, second, third, fourth connecting parts 87-3, 97-3, 113-3, 115-3 of one of the fingers 80A-3, 80B-3 is changed from that of the other finger, the flexing conditions may be different between the fingers 80A-3 and 80B-3 even before the object comes in contact with the fingers 80A-3, 80B-3.

While the embodiments of the present invention have been described above, the present invention is not limited to the particular embodiments and various changes and modifications may be made within the scope of technical idea as described in the appended claims, specification and drawings. It should be noted that any configuration and structure achieving the function and effect of the present invention, even though it is not illustrated directly in the specification and the drawings, is also within the scope of the technical idea of the present invention. For example, though the aforementioned hand 1 (1-2, 1-3) is composed of two fingers, the hand may be composed of three or more fingers. Also in this case, the respective fingers may be moved differently from each other by driving with a single driving mechanism. This makes the movement further similar to the movement of a plurality of fingers of a human hand easy.

Further, though the fourth connecting part 115-3 is designed such that a part thereof enters into the opening 85-3 of the first digital part 81-3 in the aforementioned hand 1-3, the fourth connecting part 115-3 may be designed such that the entire thereof enters into the opening 85-3 of the first digital part 81-3. In a case of the aforementioned hand 1-3, the two fingers 80A-3, 80B-3 are driven simultaneously by the single mechanism 30-3 via the single linkage member 50-3, the fingers 80A-3, 80B-3 may be driven separately by respective driving mechanisms. The power of the linear actuator 31-3 may be transferred to the third connecting part 113-3 by any member (e.g. a linear guide) other than the linkage member 50-3.

INDUSTRIAL APPLICABILITY

The present invention may be applied for uses for flexing a plurality of articulated mechanisms separately differently according to an object to be grasped.

EXPLANATION OF REFERENCES

1-1 (1-2, 1-3) hand
10 (10-2, 10-3) mounting member
30 (30-2, 30-3) driving mechanism
31 (31-2, 31-3) linear actuator (driving mechanism)
40 (40-2) linkage member (driving mechanism)
50-3 linkage member (driving mechanism)
80A, B (80A-2, B-2, 80A-3, B-3) finger
81 (81-2, 81-3) first digital part
82-3 lower surface
83-3 side wall portion
87 (87-2, 87-3) first connecting part
91 (91-2, 91-3) second digital part
92-3 lower surface
93-3 side wall portion
93a-3 back-side edge
931-3 sixth connecting part cutout
97 (97-2, 97-3) second connecting part
101 (101-2, 101-3) third digital part
107 (107-2, 107-3) fifth connecting part
111 (111-2, 111-3) first driving part
113 (113-2, 113-3) third connecting part
115 (115-2, 115-3) fourth connecting part
121 (121-2, 121-3) second driving part
123 (123-2, 123-3) sixth connecting part
125 (125-2, 125-3) seventh connecting part

What is claimed is:

1. An articulated mechanism system comprising a plurality of articulated mechanisms, each articulated mechanism having:
   a mounting member;
   a first digital part of which proximal end portion is rotatably connected to said mounting member by a first connecting part;
   a second digital part of which proximal end portion is rotatably connected to a distal end portion of said first digital part by a second connecting part;
   a third digital part of which proximal end portion is rotatably connected to a distal end portion of said second digital part by a fifth connecting part;
   a first driving part of which distal end portion is rotatably connected to a proximal end portion of said second digital part by a fourth connecting part and of which proximal end portion is connected to a third connecting part for applying driving power; and
   a second driving part of which distal end portion is rotatably connected to a proximal end portion of said third digital part by a seventh connecting part and of which proximal end portion is rotatably connected to a distal end portion of said first driving part by a sixth connecting part or to a distal end portion of said first digital part by a sixth connecting part, said sixth connecting part being disposed on a portion between the second connecting part and the distal end of said first digital part and is inserted into a sixth connecting part cutout formed in each back-side edge of right and left side wall portions of the second digital part,
   wherein by extruding said third connecting part toward said fourth connecting part, said first digital part and said second digital part are integrally rotated about said first connecting part or the second digital part is rotated about the second connecting part when the rotation of the first digital part is blocked,
   wherein when said second digital part is rotated relative to said first digital part, said third digital part is rotated relative to said second digital part by said second driving part,
   wherein when the third digital part is flexed inwardly relative to the second digital part, said sixth connecting part gets out of said sixth connecting part cutout, and
   wherein said plurality of articulated mechanisms are arranged in parallel to each other, and said articulated mechanism system further comprises a single driving mechanism for driving said third connecting parts of said respective articulated mechanisms for the same distance and in the same direction so that said plurality of articulated mechanisms are driven at a time.

2. An articulated mechanism system as claimed in claim 1, wherein said second connecting part for connecting said second digital part to said first digital part is located on the inside of said fourth connecting part for connecting said first driving part to said second digital part.

3. An articulated mechanism system as claimed in claim 2, wherein said driving mechanism comprises a linkage member which is linked to said respective third connecting parts to reciprocatably move said third connecting parts at a time, and an actuator for driving said linkage member.

4. A hand comprising an articulated mechanism system as claimed in claim 2.

5. An articulated mechanism system as claimed in claim 1, wherein at least one of said first, second, third, and fourth connecting parts of one of the articulated mechanisms has a position different from that of the other articulated mechanism(s).

6. An articulated mechanism system as claimed in claim 5, wherein said driving mechanism comprises a linkage member which is linked to said respective third connecting parts to reciprocatably move said third connecting parts at a time, and an actuator for driving said linkage member.

7. A hand comprising an articulated mechanism system as claimed in claim 5.

8. An articulated mechanism system as claimed in claim 1, wherein said driving mechanism comprises a linkage member which is linked to said respective third connecting parts to reciprocatably move said third connecting parts at a time, and an actuator for driving said linkage member.

9. A hand comprising an articulated mechanism system as claimed in claim 8.

10. A hand comprising an articulated mechanism system as claimed in claim 1.

11. An articulated mechanism system as claimed in claim 1, wherein said driving mechanism comprises a linkage member which is linked to said respective third connecting parts to reciprocatably move said third connecting parts at a time, and an actuator for driving said linkage member.

12. A hand comprising the articulated mechanism system as claimed in claim 1.

13. An articulated mechanism comprising:
a mounting member;
a first digital part of which proximal end portion is rotatably connected to said mounting member by a first connecting part;
a second digital part of which proximal end portion is rotatably connected to a distal end portion of said first digital part by a second connecting part;
a third digital part of which proximal end portion is rotatably connected to a distal end portion of said second digital part by a fifth connecting part;
a first driving part of which distal end portion is rotatably connected to a proximal end portion of said second digital part by a fourth connecting part and of which proximal end portion is connected to a third connecting part for applying driving power; and
a second driving part of which distal end portion is rotatably connected to a proximal end portion of said third digital part by a seventh connecting part and of which proximal end portion is rotatably connected to a distal end portion of said first driving part by a sixth connecting part or to a distal end portion of said first digital part by a sixth connecting part, said sixth connecting part being disposed on a portion between the second connecting part and the distal end of said first digital part and is inserted into a sixth connecting part cutout formed in each back-side edge of right and left side wall portions of the second digital part,
wherein by extruding said third connecting part toward said fourth connecting part, said first digital part and said second digital part are integrally rotated about said first connecting part or the second digital part is rotated about the second connecting part when the rotation of the first digital part is blocked,
wherein when said second digital part is rotated relative to said first digital part, said third digital part is rotated relative to said second digital part by said second driving part,
wherein when the third digital part is flexed inwardly relative to the second digital part, said sixth connecting part gets out of said sixth connecting part cutout,
wherein said first and second digital parts are each made of a plate formed in a U-like shape and are arranged such that lower surfaces of bottoms thereof face to the inside,
wherein said fourth connecting part is disposed on a portion between said second connecting part and the proximal end of said second digital part, and
wherein at least a part of said fourth connecting part enters into an opening formed in the outside of said first digital part and said fourth connecting part is exposed outwardly from the opening of the first digital part when the second digital part is flexed inwardly relative to the first digital part.

14. An articulated mechanism as claimed in claim 13, wherein said third digital part is made of a plate formed in a U-like shape and is arranged such that a lower surface of a bottom thereof faces to the inside.

15. A finger comprising an articulated mechanism as claimed in claim 13.

16. A hand comprising a plurality of fingers as claimed in claim 15.

17. An articulated mechanism as claimed in claim 13, wherein when the third digital part is flexed inwardly relative to the second digital part, the seventh connecting part enters into a seventh connecting part cutout formed in each inside edge of right and left side wall portions of the second digital part at a position on the proximal side from the fifth connecting part.

18. An articulated mechanism as claimed in claim 17, wherein on the side of the back-side edge of the second digital part, a portion from the sixth connecting part cutout to the proximal end is lower than the other portion from the sixth connecting part cutout to the distal end, and
wherein on the side of the inside edge of the second digital part, a portion from the seventh connecting part cutout to the distal end is higher than the other portion from the seventh connecting part cutout to the proximal end.

19. A hand comprising:
a mounting member;
a driving mechanism attached to the mounting member; and
a pair of fingers mounted to the mounting member via a linkage member and driven by the driving mechanism,
wherein each of the fingers has an articulated mechanism having a first digital part of which proximal end portion is rotatably connected to the mounting member by a first connecting part, a second digital part of which proximal end portion is rotatably connected to a distal end portion of the first digital part by a second connecting part, and a first driving part of which distal end portion is rotatably connected to a proximal end portion of the second digital part by a fourth connecting part and of which proximal end portion is connected to a third connecting part for applying driving power, wherein by extruding the third connecting part toward the fourth connecting part, the first digital part and the second digital part are driven together so that the first digital part and the second digital part are integrally rotated about the first connecting part or the second digital part is rotated about the second connecting part when the rotation of the first digital part is blocked, wherein the linkage member has a first connecting part shaft, a third connecting part shaft, and a connecting rod which are attached to corners of a triangular shape as seen from the side of the linkage member, respectively, wherein the connecting rod is connected to the driving mechanism, the first connecting part shaft is rotatably attached to the mounting member, and the first connecting parts of a pair of the first digital parts are rotatably attached to the both ends of the first connecting part shaft, respectively, wherein the third connecting parts of a pair of the first driving parts are rotatably attached to both ends of the third connecting part shaft, respectively, and wherein the linkage member is rotated about the first connecting part by the driving mechanism so as to extrude the third connecting part toward the fourth connecting part, thereby driving simultaneously the pair of fingers.

20. A hand as claimed in claim 19, wherein the connecting rod is rotatably disposed between a pair of side walls of the linkage member, and a rod retractably projecting from the driving mechanism is attached to a middle of the connecting rod, whereby the two fingers are driven by the single driving mechanism via the single linkage member.

21. A hand as claimed in claim 19, wherein the linkage member has a first connecting part shaft rotatably inserted in a lower portion of the linkage member, a third connecting part shaft rotatably inserted in an upper portion of one of biforked portions of the linkage member, further the connecting rod disposed on upper portions of the other biforked portion of the linkage member.

22. A hand as claimed in claim 19, wherein the both end portions of the first connecting part shaft are rotatably attached to the mounting member and the first connecting parts of the first digital parts are rotatably disposed on the both ends of the first connecting part shaft projecting outside of the mounting member after the penetration, respectively.

* * * * *